(12) United States Patent
Lalleman et al.

(10) Patent No.: US 10,524,992 B2
(45) Date of Patent: *Jan. 7, 2020

(54) HAIR DYEING PROCESS USING AT LEAST ONE DIRECT AND/OR NATURAL DYE, A TITANIUM SALT, A CELLULOSE-BASED POLYSACCHARIDE AND OPTIONALLY A PARTICULAR ORGANIC SOLVENT

(71) Applicant: L'OREAL, Paris (FR)

(72) Inventors: Boris Lalleman, Paris (FR); Alain Lagrange, Coupvray (FR); Françoise Albouy, Rueil Malmaison (FR); Frédéric Simonet, Clichy (FR)

(73) Assignee: L'OREAL, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/534,283

(22) PCT Filed: Dec. 7, 2015

(86) PCT No.: PCT/EP2015/078844

§ 371 (c)(1),
(2) Date: Jun. 8, 2017

(87) PCT Pub. No.: WO2016/091814

PCT Pub. Date: Jun. 16, 2016

(65) Prior Publication Data

US 2017/0333312 A1   Nov. 23, 2017

(30) Foreign Application Priority Data

Dec. 8, 2014 (FR) ..................................... 14 62061

(51) Int. Cl.
| | | |
|---|---|---|
| *A61Q 5/10* | (2006.01) | |
| *A61K 8/29* | (2006.01) | |
| *A61K 8/41* | (2006.01) | |
| *A61K 8/49* | (2006.01) | |
| *A61K 8/73* | (2006.01) | |
| *A45D 40/24* | (2006.01) | |
| *A61K 8/19* | (2006.01) | |
| *A61K 8/22* | (2006.01) | |
| *A61K 8/34* | (2006.01) | |
| *A61K 8/365* | (2006.01) | |
| *A61K 8/44* | (2006.01) | |
| *A61K 8/72* | (2006.01) | |

(52) U.S. Cl.
CPC ................ *A61K 8/29* (2013.01); *A45D 40/24* (2013.01); *A61K 8/19* (2013.01); *A61K 8/22* (2013.01); *A61K 8/34* (2013.01); *A61K 8/365* (2013.01); *A61K 8/418* (2013.01); *A61K 8/44* (2013.01); *A61K 8/498* (2013.01); *A61K 8/72* (2013.01); *A61K 8/731* (2013.01); *A61K 8/732* (2013.01); *A61Q 5/10* (2013.01); *A61K 2800/4324* (2013.01); *A61K 2800/87* (2013.01)

(58) Field of Classification Search
CPC . A61Q 5/10; A61Q 5/065; A61K 8/29; A61K 8/368; A61K 8/418; A61K 8/498; A61K 8/731; A61K 8/58; A61K 8/602; A61K 2800/4324

See application file for complete search history.

(56) References Cited

U.S. PATENT DOCUMENTS

| | | |
|---|---|---|
| 2,798,053 A | 7/1957 | Brown |
| 2,923,692 A | 2/1960 | Ackerman et al. |
| 3,376,110 A | 4/1968 | Shiraeff |
| 3,915,921 A | 10/1975 | Schlatzer, Jr. |
| 4,003,699 A | 1/1977 | Rose et al. |
| 4,131,576 A | 12/1978 | Iovine et al. |
| RE30,199 E | 1/1980 | Rose et al. |
| 4,237,243 A | 12/1980 | Quack et al. |
| 4,509,949 A | 4/1985 | Huang et al. |
| 4,823,985 A | 4/1989 | Grollier et al. |
| 5,008,093 A | 4/1991 | Merianos |
| 5,061,289 A | 10/1991 | Clausen et al. |
| 5,183,901 A | 2/1993 | Login et al. |
| 5,380,340 A | 1/1995 | Neunhoeffer et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

STIC Search Report dated Nov. 25, 2016 filed in U.S. Appl. No. 15/104,121.*
International Search Report for PCT/EP2015/078558, dated Mar. 15, 2016.
International Search Report for PCT/EP2015/078844, dated Jan. 27, 2016.

(Continued)

*Primary Examiner* — Eisa B Elhilo
(74) *Attorney, Agent, or Firm* — The Marbury Law Group, PLLC

(57) ABSTRACT

The present invention relates to a process for dyeing keratin fibres, in particular human keratin fibres such as the hair, in which said fibres are treated using one or more cosmetic compositions comprising a) one or more dyes chosen from synthetic direct dyes and dyes of natural origin, b) one or more titanium salts and b1) optionally one or more particular carboxylic acids, c) one or more cellulose-based polysaccharides, d) optionally one or more organic compounds that are liquid at 25° C., with a Hansen solubility parameter value $\delta H<16$ $(MPa)^{1/2}$ at 25° C., e) optionally one or more chemical oxidizing agents such as hydrogen peroxide or one or more hydrogen peroxide-generating systems.

15 Claims, No Drawings

(56) References Cited

U.S. PATENT DOCUMENTS

| | | |
|---|---|---|
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |
| 6,099,592 A | 8/2000 | Vidal et al. |
| 6,120,780 A | 9/2000 | Dupuis et al. |
| 6,284,003 B1 | 9/2001 | Rose et al. |
| 6,730,789 B1 | 5/2004 | Birault et al. |
| 7,081,485 B2 | 7/2006 | Suh et al. |
| 7,833,290 B2 | 11/2010 | Guerin et al. |
| 10,010,495 B2 * | 7/2018 | Lalleman ............... A61K 8/362 |
| 2003/0103917 A1 | 6/2003 | Pruche |
| 2003/0163877 A1 | 9/2003 | Baker et al. |
| 2003/0163878 A1 | 9/2003 | Pruche |
| 2004/0172771 A1 | 9/2004 | Collard et al. |
| 2005/0086745 A1 | 4/2005 | Kravtchenko et al. |
| 2006/0260069 A1 | 11/2006 | Legrand |
| 2006/0265818 A1 | 11/2006 | Seiler et al. |
| 2006/0272103 A1 | 12/2006 | Barbarat |
| 2008/0233068 A1 * | 9/2008 | Forbes .................... A61K 8/25 424/70.1 |
| 2009/0151089 A1 | 6/2009 | Audousset |
| 2009/0151090 A1 | 6/2009 | Audousset |
| 2010/0146718 A1 | 6/2010 | Guerin et al. |
| 2010/0154143 A1 * | 6/2010 | Guerin .................... A61K 8/19 8/424 |
| 2010/0192969 A1 | 8/2010 | DeGeorge et al. |
| 2011/0209294 A1 | 9/2011 | Choi |
| 2012/0110751 A1 | 5/2012 | Blackburn et al. |
| 2013/0139846 A1 | 6/2013 | Rondot et al. |
| 2013/0263389 A1 | 10/2013 | Lalleman et al. |
| 2014/0318555 A1 * | 10/2014 | Borschke ................ A24B 1/02 131/303 |

FOREIGN PATENT DOCUMENTS

| | | |
|---|---|---|
| DE | 4133957 A1 | 4/1993 |
| DE | 19543988 A1 | 5/1997 |
| DE | 19859721 A1 | 6/2000 |
| EP | 0173109 A2 | 3/1986 |
| EP | 0216479 A1 | 4/1987 |
| EP | 0503853 A2 | 9/1992 |
| EP | 0714954 A2 | 6/1996 |
| EP | 0770375 A1 | 5/1997 |
| EP | 0815828 A1 | 1/1998 |
| EP | 1426039 A1 | 6/2004 |
| EP | 1707182 A1 | 10/2006 |
| EP | 2060301 A2 | 5/2009 |
| EP | 2062615 A2 | 5/2009 |
| EP | 2196188 A2 | 6/2010 |
| EP | 2438900 A1 | 4/2012 |
| FR | 3526723 A1 | 9/1979 |
| FR | 2416913 A1 | 3/1987 |
| FR | 2633940 A1 | 1/1990 |
| FR | 2733749 A1 | 11/1996 |
| FR | 2801308 A1 | 5/2001 |
| FR | 2814943 A1 | 4/2002 |
| FR | 2814945 A1 | 4/2002 |
| FR | 2814946 A1 | 4/2002 |
| FR | 2814947 A1 | 4/2002 |
| FR | 2886136 A1 | 12/2006 |
| FR | 2928086 A1 | 9/2009 |
| FR | 2951374 A1 | 4/2011 |
| FR | 2976793 A1 | 12/2012 |
| FR | 2976797 A1 | 12/2012 |
| FR | 2981570 A1 | 4/2013 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 2006/106366 A1 | 10/2006 |
| WO | 2010/133573 A2 | 11/2010 |
| WO | 2010/135237 A1 | 11/2010 |
| WO | 2011/000892 A2 | 1/2011 |
| WO | 2011/045404 A2 | 4/2011 |
| WO | 2011/086282 A1 | 7/2011 |
| WO | 2011/086284 A1 | 7/2011 |
| WO | 2011/086285 A1 | 7/2011 |
| WO | 2012/175683 A2 | 12/2012 |
| WO | 2015/086677 A1 | 6/2015 |
| WO | 2015/086678 A1 | 6/2015 |
| WO | 2016/091720 A1 | 6/2016 |
| WO | 2016/091721 A1 | 6/2016 |
| WO | 2016/091817 A1 | 6/2016 |

OTHER PUBLICATIONS

International Search Report for PCT/EP2015/078560, dated Feb. 1, 2016.
International Search Report for PCT/EP2015/078847, dated Mar. 11, 2016.
Final Office Action for copending U.S. Appl. No. 15/534,268, dated Jan. 31, 2019.
Non-Final Office Action for copending U.S. Appl. No. 15/534,268, dated Jul. 19, 2018.
Non-Final Office Action for copending U.S. Appl. No. 15/534,290, dated Jul. 19, 2018.
Non-Final Office Action for copending U.S. Appl. No. 15/534,296, dated Jul. 19, 2018.
Final Office Action for co-pending U.S. Appl. No. 15/534,290, dated March 22, 2019.
Final Office Action for co-pending U.S. Appl. No. 15/534,296, dated March 22, 2019.
International Search Report for counterpart Application No. PCT/EP2014/077224, dated Mar. 11, 2015.
International Search Report for counterpart Application No. PCT/EP20141077225, dated Mar. 11, 2015.
Non-Final Office Action for U.S. Appl. No. 15/104,121, dated Mar. 27, 2017 (now U.S. Pat. No. 10,010,495).
Non-Final Office Action for U.S. Appl. No. 15/104,131, dated Mar. 27, 2017 (now U.S. Pat. No. 10,052,273).
Final Office Action for U.S. Appl. No. 15/104,121, dated Oct. 24, 2017 (now U.S. Pat. No. 10,010,495).
Final Office Action for U.S. Appl. No. 15/104,131, dated Oct. 24, 2017 (now U.S. Pat. No. 10,052,273).
Notice of Allowance for U.S. Appl. No. 15/104,121, dated Mar. 19, 2018 (now U.S. Pat. No. 10,010,495).
Notice of Allowance for U.S. Appl. No. 15/104,131, dated May 1, 2018 (now U.S. Pat. No. 10,052,273).
Non-Final Office Action for co-pending U.S. Appl. No. 15/534,268, dated Jul. 31, 2019.
Notice of Allowance for co-pending U.S. Appl. No. 15/534,290, dated Sep. 3, 2019.
Notice of Allowance for co-pending U.S. Appl. No. 15/534,296, dated Sep. 5, 2019.

* cited by examiner

HAIR DYEING PROCESS USING AT LEAST ONE DIRECT AND/OR NATURAL DYE, A TITANIUM SALT, A CELLULOSE-BASED POLYSACCHARIDE AND OPTIONALLY A PARTICULAR ORGANIC SOLVENT

CROSS REFERENCE TO RELATED APPLICATIONS

This is a national stage application of PCT/EP2015/078844, filed internationally on Dec. 7, 2015, which claims priority to French Application No. 1462061, filed on Dec. 8, 2014, both of which are incorporated by reference herein in their entireties.

The present invention relates to a process for dyeing keratin fibres, in particular human keratin fibres such as the hair, in which said fibres are treated using one or more cosmetic compositions comprising a) one or more synthetic direct dyes and/or dyes of natural origin, b) one or more titanium salts and b1) optionally one or more particular carboxylic acids, c) one or more cellulose-based polysaccharides, d) optionally one or more organic compounds that are liquid at 25° C., with a Hansen solubility parameter value δH<16 (MPa)$^{1/2}$ at 25° C., e) optionally one or more chemical oxidizing agents such as hydrogen peroxide or one or more hydrogen peroxide-generating systems.

It is known practice to dye keratin fibres and in particular human hair with dye compositions containing direct dyes. The standard dyes that are used are, in particular, dyes of the nitrobenzene, anthraquinone, nitropyridine, azo, xanthene, acridine, azine or triarylmethane type, or natural dyes.

These dyes may be nonionic, anionic, cationic or amphoteric. These dyes are coloured or colouring molecules that have affinity for keratin fibres. These compositions containing one or more direct dyes are applied to keratin fibres for a time necessary to obtain the desired colouring, and are then rinsed out. The colourings that result therefrom are particularly chromatic colourings but are, however, only temporary or semi-permanent since the nature of the interactions that bind the direct dyes to the keratin fibre and their desorption from the surface and/or the core of the fibre are responsible for their weak dyeing power and their poor persistence with respect to light, washing or perspiration.

Progress therefore remains to be made in this field in order to afford powerful, resistant dyeing results that respect the nature of the hair using compositions containing dyes that are especially natural.

In the field of dyeing using natural extracts such as ortho-diphenols (ODPs), it is also known practice to dye keratin materials such as the hair or the skin using ODPs in the presence of a metal salt especially of manganese (Mn) and/or zinc (Zn). In particular, patent applications FR 2 814 943, FR 2 814 945, FR 2 814 946 and FR 2 814 947 propose compositions for dyeing the skin or keratin fibres, comprising a dye precursor that contains at least one ortho-diphenol, Mn and/or Zn oxides and salts, alkaline agents of hydrogen carbonate type in a particular Mn, Zn/hydrogen carbonate ratio and optionally an enzyme. According to these documents, it is possible to obtain colourings of keratin materials with atmospheric oxygen or any oxygen-generating system.

However, the colourings obtained using ODPs are not strong enough or intense enough, and/or are not very persistent, especially in the case of hair fibres.

It is known practice to use metals at acidic pH for dyeing keratin fibres in amounts similar to those employed for dyes using a mordanting process, which consists in preparing the fibres before performing the dyeing operation in order to obtain persistent shades (*Ullmann's Encyclopaedia* "Metal and Dyes", 2005 § 5.1, p. 8). However, this process generally has the drawback of not always respecting the cosmetic nature of the keratin fibre.

Other documents describe the use of ODPs in combination with Mn and Zn salts and other metal salts, including titanium salts, and a chemical oxidizing agent (FR 297 673, WO2011/086284, WO2011/086282 and FR 2 951 374).

Nevertheless, improvements should be further made, especially in terms of persistence of the colour with regard to shampooing and to sweat.

There is thus a real need to develop dyeing processes that make it possible to obtain more powerful and/or more persistent colourings using synthetic direct dyes and/or dyes of natural origin, in particular ODPs, preferably using natural extracts that are rich in ODPs, less aggressive to keratin fibres, or that require smaller amounts of dyes. More particularly, there is a need to obtain colourings that satisfactorily withstand external agents (light, bad weather, shampooing or sweat), which are persistent and homogeneous, i.e. showing little dyeing selectivity between the root and the end, while at the same time remaining strong and/or chromatic. In addition, it is necessary, in order to obtain satisfactory dyeing performance, for the product to be stable and to have suitable working qualities, i.e. a sufficient rheology so as not to run during the leave-on time. For this, it is preferable for the dye support not to interact in the dyeing process.

This (these) aim(s) are achieved by the present invention, one subject of which is a process for dyeing keratin fibres, in particular human keratin fibres such as the hair, in which said fibres are treated, in one or more steps, with one or more cosmetic compositions containing, taken together or separately in said composition(s), the following ingredients:

a) one or more dyes chosen from synthetic direct dyes and dyes of natural origin, preferably chosen from ODPs;

b) one or more titanium salts; in particular, the Ti atom of the salt is of oxidation state 2, 3 or 4, denoted Ti(II), Ti(III) or Ti(IV), preferably Ti(IV);

b1) optionally one or more carboxylic acids of formula (I) below:

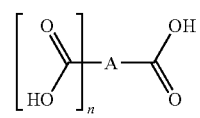

(I)

formula (I) or a salt thereof, in which:

A represents a saturated or unsaturated, cyclic or non-cyclic and aromatic or non-aromatic hydrocarbon-based group, which is monovalent when n has the value 0 or polyvalent when n is greater than or equal to 1, comprising from 1 to 50 carbon atoms, which is optionally interrupted with one or more heteroatoms and/or optionally substituted, especially with one or more hydroxyl groups; preferably, A represents a monovalent ($C_1$-$C_6$)alkyl group or a polyvalent ($C_1$-$C_6$)alkylene group optionally substituted with one or more hydroxyl groups;

n represents an integer between 0 and 10 inclusive; preferably, n is between 0 and 5, such as between 0 and 2;

c) one or more cellulose-based polysaccharides;
d) optionally one or more organic compounds that are liquid at 25° C. with a Hansen solubility parameter value δH of less than 16 (MPa)$^{1/2}$ at 25° C.; and
e) optionally one or more chemical oxidizing agents chosen in particular from hydrogen peroxide or one or more hydrogen peroxide-generating systems.

Preferably, the composition(s) used in the process of the invention are aqueous.

Another subject of the invention is a cosmetic composition comprising ingredients a), b), c), optionally d) and optionally e), as defined previously.

Another subject of the present invention relates to a multi-compartment device comprising ingredients a), b), c), optionally d) and optionally e), distributed in several compartments.

The multi-compartment device or "kit" is suitable for performing the dyeing process according to the invention.

The process according to the invention has the advantage of dyeing human keratin fibres, with persistent dyeing results. In particular, the dyeing process according to the invention can produce colourings that are resistant to washing, perspiration, sebum and light without impairing the fibres. The resistance to perspiration is particularly good. Furthermore, the dyeing process used can induce a satisfactory "build-up" and/or strength of the colouring.

Other subjects, characteristics, aspects and advantages of the present invention will emerge even more clearly on reading the description and the examples that follow.

a) Dye(s)

In accordance with the present invention, the dyeing process uses a) one or more synthetic direct dyes and/or dyes of natural origin.

The dye(s) of the invention may be present in one or more cosmetic compositions used during the dyeing process.

According to a particular embodiment of the invention, the dye(s) are chosen from synthetic direct dyes.

The synthetic direct dye(s) that may be used in the context of the invention may be chosen from fluorescent or non-fluorescent, anionic, cationic or neutral direct dyes.

These synthetic direct dyes are chosen in particular from those conventionally used in direct dyeing, any commonly used aromatic and/or non-aromatic dyes such as neutral, acidic or cationic nitrobenzene direct dyes, neutral, acidic or cationic azo direct dyes, natural direct dyes, neutral, acidic or cationic quinone and in particular anthraquinone direct dyes, azine, polyarylmethane such as triarylmethane, indoamine, polymethine such as styryl, porphyrin, metalloporphyrin, phthalocyanine, methine cyanine direct dyes.

According to a particular embodiment of the invention, the dye(s) are chosen from anionic direct dyes. These dyes are commonly referred to as "acidic" direct dyes or "acid dyes" on account of their affinity for alkaline substances. The term "anionic direct dyes" means any direct dye comprising in its structure at least one $CO_2R$ or $SO_3R$ substituent with R denoting a hydrogen atom or a cation originating from a metal or an amine, or an ammonium ion. The anionic dyes may be chosen from acidic nitro direct dyes, acidic azo dyes, acidic azine dyes, acidic triarylmethane dyes, acidic indoamine dyes, acidic anthraquinone dyes, indigoid dyes and acidic natural dyes.

According to another particular embodiment of the invention, the dye(s) are chosen from cationic direct dyes or dyes commonly referred to as "basic" direct dyes or "basic dyes" on account of their affinity for acidic substances. The cationic dyes are preferentially chosen from hydrazono, (poly) azo, polymethine such as styryl and (poly)arylmethane dyes.

More preferentially, the cationic dye(s) of the invention are chosen from the hydrazono dyes of formulae (Va) and (V'a), the azo dyes (VIa) and (VI'a) and the diazo dyes (VIIa) below:

(Va)

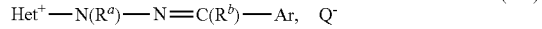
(V'a)

(VIa)

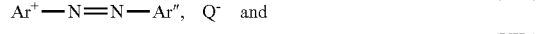
(VI'a)

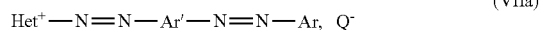
(VIIa)

formulae (Va), (V'a), (VIa), (VI'a) and (VIIa) with:

Het$^+$ representing a cationic heteroaryl radical, preferentially bearing an endocyclic cationic charge, such as imidazolium, indolium or pyridinium, optionally substituted, preferentially with one or more ($C_1$-$C_8$) alkyl groups such as methyl;

Ar$^+$ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more ($C_1$-$C_8$)alkyl, hydroxyl or ($C_1$-$C_8$)alkoxy groups;

Ar" is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

R$^a$ and R$^b$, which may be identical or different, represent a hydrogen atom or a ($C_1$-$C_8$)alkyl group, which is optionally substituted, preferentially with a hydroxyl group;

or alternatively the substituent R$^a$ with a substituent of Het$^+$ and/or R$^b$ with a substituent of Ar and/or R$^a$ with R$^b$ form, together with the atoms that bear them, a (hetero)cycloalkyl;

particularly, R$^a$ and R$^b$ represent a hydrogen atom or a ($C_1$-$C_4$)alkyl group, which is optionally substituted with a hydroxyl group;

Q$^-$ represents an anionic counterion as defined previously.

According to a preferred variant of the invention, the cationic dyes are chosen from the polymethine dyes of formulae (VIIIa) and (VIII'a) below:

(VIIIa)

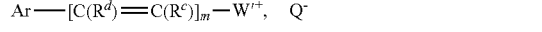
(VIII'a)

formulae (VIIIa) or (VIII'a) with:
- $W^+$ representing a cationic heterocyclic or heteroaryl group, particularly comprising a quaternary ammonium optionally substituted with one or more $(C_1-C_8)$alkyl groups optionally substituted especially with one or more hydroxyl groups;
- $W'^+$ representing a heterocyclic or heteroaryl radical as defined for W+;
- Ar representing a (hetero)aryl group such as phenyl or naphthyl, optionally substituted preferentially with i) one or more halogen atoms such as chlorine or fluorine; ii) one or more $(C_1-C_8)$alkyl groups, preferably of $C_1-C_4$ such as methyl; iii) one or more hydroxyl groups; iv) one or more $(C_1-C_8)$alkoxy groups such as methoxy; v) one or more hydroxy$(C_1-C_8)$alkyl groups such as hydroxyethyl, vi) one or more amino groups or (di)$(C_1-C_8)$alkylamino, preferably with the $C_1-C_4$ alkyl part optionally substituted with one or more hydroxyl groups, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;
- Ar' is a (hetero)aryl radical as defined for Ar;
- m' represents an integer between 1 and 4 inclusive, and in particular m has the value 1 or 2; more preferentially 1;
- $R^c$, $R^d$, which may be identical or different, represent a hydrogen atom or an optionally substituted $(C_1-C_8)$ alkyl group, preferentially of $C_1-C_4$, or alternatively $R^c$ contiguous with $W^+$ or $W'^+$ and/or $R^d$ contiguous with Ar or Ar' and/or contiguous $R^c$ and $R^d$ form, with the atoms that bear them, a (hetero)cycloalkyl, particularly $R^c$ is contiguous with $W^+$ or $W'^+$ and forms a (hetero)cycloalkyl such as cyclohexyl;
- $Q^-$ as defined previously preferably represents a halide or a mesylate.

Mention may be made more particularly of the azo and hydrazono dyes bearing an endocyclic cationic charge of formulae (Va), (V'a), (VIa) and (VI'a) as defined previously. More particularly those of formulae (Va), (V'a) and (VIa) derived from the dyes described in patent applications WO 95/15144, WO 95/01772 and EP-714954. Preferentially, the cationic dyes comprise an endocyclic cationic charge and have the following formula:

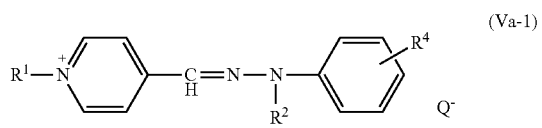

(Va-1)

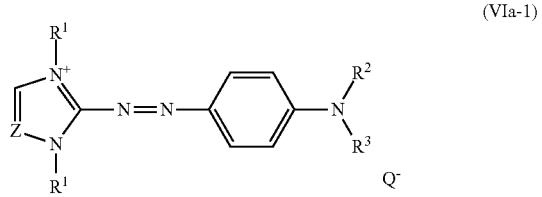

(VIa-1)

formulae (Va-1) and (Via-1) with:
- $R^1$ representing a $(C_1-C_4)$alkyl group such as methyl;
- $R^2$ and $R^3$, which may be identical or different, represent a hydrogen atom or a $(C_1-C_4)$alkyl group, such as methyl; and
- $R^4$ represents a hydrogen atom or an electron-donating group such as optionally substituted $(C_1-C_8)$alkyl, optionally substituted $(C_1-C_8)$alkoxy, or (di)$(C_1-C_8)$(alkyl)amino optionally substituted on the alkyl group(s) with a hydroxyl group; particularly, $R^4$ is a hydrogen atom;
- Z represents a CH group or a nitrogen atom, preferentially CH;
- $Q^-$ as defined previously preferably represents a halide or a mesylate.

Particularly, the dyes of the invention are chosen from those of formula (IIIa-1) and (IVa-1) is chosen from Basic Red 51, Basic Yellow 87 and Basic Orange 31 or derivatives thereof:

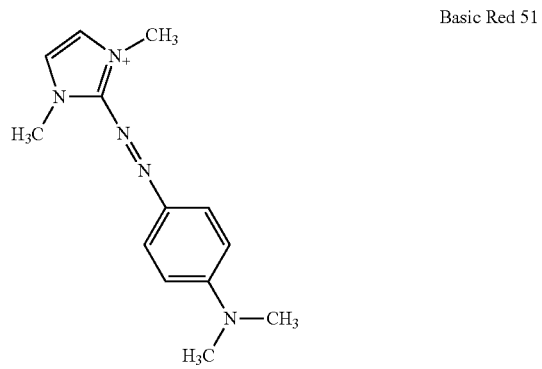

Basic Red 51

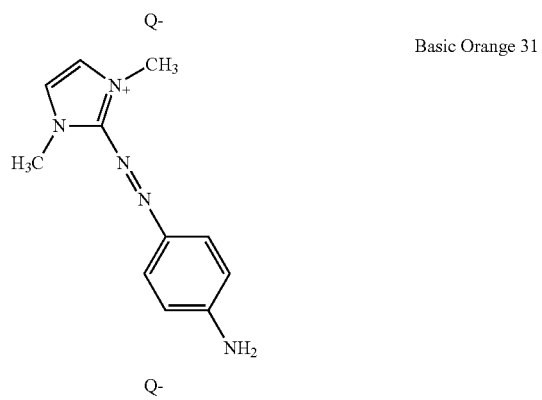

Basic Orange 31

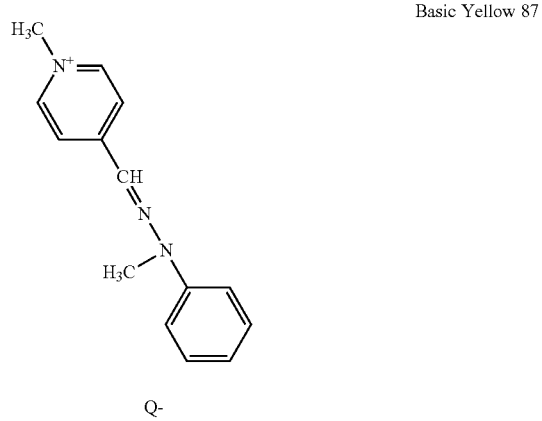

Basic Yellow 87 with $Q^-$ as defined previously preferably representing a halide or a mesylate.

According to a particularly advantageous embodiment of the invention, the dye(s) are chosen from dyes of natural origin or "natural" dyes.

Among the natural dyes, mention may be made of lawsone, juglone, indigo, isatin, curcumin, chlorophyllin, laccaic acid, kermesic acid, carminic acid, sorghum, spinulosin, apigenidin, orceins, polyphenols or ortho-diphenols (ODPs) and any extract rich in ODPs. Use may also be made of extracts or decoctions comprising these natural dyes and especially henna-based and/or indigo-based extracts or poultices.

According to a particularly preferred embodiment of the invention, the dye(s) are chosen from ortho-diphenol(s) or ODP(s).

The invention relates to one or more ODPs or mixtures of compounds comprising one or more aromatic rings, at least one of which is a benzene ring substituted with at least two hydroxyl (OH) groups borne by two adjacent carbon atoms of said benzene group being present in the structure of the ortho-diphenol(s).

The aromatic ring is more particularly a fused aryl or fused heteroaromatic ring, i.e. optionally comprising one or more heteroatoms, such as benzene, naphthalene, tetrahydronaphthalene, indane, indene, anthracene, phenanthrene, indole, isoindole, indoline, isoindoline, benzofuran, dihydrobenzofuran, chroman, isochroman, chromene, isochromene, quinoline, tetrahydroquinoline and isoquinoline, said aromatic ring comprising at least two hydroxyl groups borne by two adjacent carbon atoms of the aromatic ring. Preferentially, the aromatic ring of the ODPs according to the invention is a benzene ring.

The term "fused ring" means that at least two saturated or unsaturated and heterocyclic or non-heterocyclic rings have a shared bond, i.e. at least one ring is placed side-by-side with another ring.

The ODP(s) according to the invention may or may not be salified. They may also be in aglycone form (without bonded sugar) or in the form of glycosylated compounds.

More particularly, the ODP(s) a) represent a compound of formula (II), or an oligomer, tautomer, optical isomer or geometrical isomer thereof, and also salts or solvates thereof, such as hydrates:

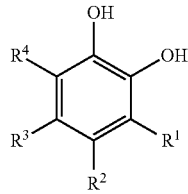

(II)

in which formula (II):
R$^1$ to R$^4$, which may be identical or different, represent: i) a hydrogen atom, ii) a halogen atom, or a group chosen from iii) hydroxyl, iv) carboxyl, v) (C$_1$-C$_{20}$)alkyl carboxylate or (C$_1$-C$_{20}$)alkoxycarbonyl, vi) optionally substituted amino, vii) optionally substituted linear or branched (C$_1$-C$_{20}$)alkyl, viii) optionally substituted linear or branched (C$_2$-C$_{20}$)alkenyl, ix) optionally substituted cycloalkyl, x) (C$_1$-C$_{20}$)alkoxy, xi) (C$_1$-C$_{20}$)alkoxy(C$_1$-C$_{20}$)alkyl, xii) (C$_1$-C$_{20}$)alkoxyaryl, xiii) aryl which can optionally be substituted, xiv) aryl, xv) substituted aryl, xvi) heterocyclic which is saturated or unsaturated, optionally bearing a cationic or anionic charge and which is optionally substituted and/or optionally fused with an aromatic ring, preferably a benzene ring, said aromatic ring optionally being substituted, in particular with one or more hydroxyl or glycosyloxy groups, xvii) a radical containing one or more silicon atoms;

or two of the substituents borne by two adjacent carbon atoms R$^1$-R$^2$, R$^2$-R$^3$ or R$^3$-R$^4$ form, together with the carbon atoms bearing them, a saturated or unsaturated and aromatic or non-aromatic ring optionally containing one or more heteroatoms and optionally fused with one or more saturated or unsaturated rings optionally containing one or more heteroatoms. In particular, the compound of formula (II) comprises from one to four rings.

A particular embodiment of the invention relates to one or more ODPs of formula (II), two adjacent substituents R$^1$-R$^2$, R$^2$-R$^3$ or R$^3$-R$^4$ of which cannot form, with the carbon atoms that bear them, a pyrrolyl radical. According to a variant, R$^2$ and R$^3$ form a pyrrolyl or pyrrolidinyl radical fused to the benzene ring bearing the two hydroxyls.

For the purposes of the present invention and unless otherwise indicated:
the saturated or unsaturated and optionally fused rings may also be optionally substituted;
the "alkyl" radicals are saturated, linear or branched, generally C$_1$-C$_{20}$, particularly C$_1$-C$_{10}$, hydrocarbon-based radicals, preferably C$_1$-C$_6$ alkyl radicals, such as methyl, ethyl, propyl, butyl, pentyl and hexyl;
the "alkenyl" radicals are unsaturated and linear or branched C$_2$-C$_{20}$ hydrocarbon-based radicals; preferably comprising at least one double bond, such as ethylene, propylene, butylene, pentylene, 2-methylpropylene and decylene;
the "aryl" radicals are monocyclic or fused or non-fused polycyclic carbon-based radicals preferentially comprising from 6 to 30 carbon atoms, at least one ring of which is aromatic; preferentially, the aryl radical is chosen from phenyl, biphenyl, naphthyl, indenyl, anthracenyl and tetrahydronaphthyl;
the "alkoxy" radicals are alkyl-oxy radicals with alkyl as defined previously, preferably C$_1$-C$_{10}$ alkyl, such as methoxy, ethoxy, propoxy and butoxy;
the "alkoxyalkyl" radicals are (C$_1$-C$_{20}$)alkoxy(C$_1$-C$_{20}$)alkyl radicals, such as methoxymethyl, ethoxymethyl, methoxyethyl, ethoxyethyl, etc.;
the "cycloalkyl" radicals are C$_4$-C$_8$ cycloalkyl radicals, preferably cyclopentyl and cyclohexyl radicals; the cycloalkyl radicals may be substituted cycloalkyl radicals, in particular substituted with alkyl, alkoxy, carboxylic acid, hydroxyl, amine and ketone groups;
the "alkyl" or "alkenyl" radicals, when they are "optionally substituted", may be substituted with at least one atom or group borne by at least one carbon atom chosen from: i) halogen; ii) hydroxyl; iii) (C$_1$-C$_2$)alkoxy; iv) (C$_1$-C$_{10}$)alkoxycarbonyl; v) (poly)hydroxy(C$_2$-C$_4$)alkoxy; vi) amino; vii) 5- or 6-membered heterocycloalkyl; viii) optionally cationic 5- or 6-membered heteroaryl, preferably imidazolium, optionally substituted with a (C$_1$-C$_4$)alkyl radical, preferably methyl; ix) amino substituted with one or two identical or different C$_1$-C$_6$ alkyl radicals optionally bearing at least: a) one hydroxyl group, b) one amino group optionally substituted with one or two optionally substituted (C$_1$-C$_3$) alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom, c) a quaternary ammonium group —N⁺R'R"R'", M⁻ for which R', R" and R'", which may be identical or different, represent a hydrogen atom or a $C_1$-$C_4$ alkyl group; and M⁻ represents the counterion of the corresponding organic acid, mineral acid or halide, d) or one optionally cationic 5- or 6-membered heteroaryl radical, preferentially imidazolium, optionally substituted with a ($C_1$-$C_4$)alkyl radical, preferably methyl; x) acylamino (—N(R)—C(O)—R') in which the R radical is a hydrogen atom or a ($C_1$-$C_4$)alkyl radical optionally bearing at least one hydroxyl group and the R' radical is a $C_1$-$C_2$ alkyl radical; a carbamoyl ((R)$_2$N—C(O)—) radical in which the R radicals, which may be identical or different, represent a hydrogen atom or a ($C_1$-$C_4$)alkyl radical optionally bearing at least one hydroxyl group; xi) alkylsulfonylamino (R'—S(O)$_2$—N(R)—) in which the R radical represents a hydrogen atom or a ($C_1$-$C_4$)alkyl radical optionally bearing at least one hydroxyl group and the R' radical represents a ($C_1$-$C_4$)alkyl radical, a phenyl radical; xii) aminosulfonyl ((R)$_2$N—S(O)$_2$—) in which the R radicals, which may be identical or different, represent a hydrogen atom or a ($C_1$-$C_4$)alkyl radical optionally bearing at least one group chosen from a) hydroxyl, b) carboxyl —C(O)—OH in the acid or salified form (preferably salified with an alkali metal or a substituted or unsubstituted ammonium); xiii) cyano; xiv) nitro; xv) carboxyl or glycosylcarbonyl; xvi) phenylcarbonyloxy optionally substituted with one or more hydroxyl groups; xvii) glycosyloxy; and phenyl group optionally substituted with one or more hydroxyl groups;

the "aryl" or "heterocyclic" radicals or the aryl or heterocyclic part of the radicals, when they are "optionally substituted", may be substituted with at least one atom or group borne by at least one carbon atom chosen from:

i) ($C_1$-$C_{10}$)alkyl, preferably $C_1$-$C_8$ alkyl, optionally substituted with one or more radicals chosen from the following radicals: hydroxyl, ($C_1$-$C_2$)alkoxy, (poly)hydroxy($C_2$-$C_4$)alkoxy, acylamino, amino substituted with two identical or different $C_1$-$C_4$ alkyl radicals optionally bearing at least one hydroxyl group or it being possible for the two radicals to form, with the nitrogen atom to which they are attached, a saturated or unsaturated and optionally substituted 5- to 7-membered, preferably 5- or 6-membered, heterocycle optionally comprising another nitrogen or non-nitrogen heteroatom; ii) halogen; iii) hydroxyl; iv) $C_1$-$C_2$ alkoxy; v) $C_1$-$C_{10}$ alkoxycarbonyl; vi) (poly)hydroxy($C_2$-$C_4$)alkoxy; vii) amino; viii) 5- or 6-membered heterocycloalkyl; ix) optionally cationic 5- or 6-membered heteroaryl, preferably imidazolium, optionally substituted with a ($C_1$-$C_4$)alkyl radical, preferably methyl; x) amino substituted with one or two identical or different $C_1$-$C_6$ alkyl radicals optionally bearing at least: a) one hydroxyl group, b) one amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom, c) one quaternary ammonium group —N⁺R'R"R'", M⁻ for which R', R" and R'", which may be identical or different, represent a hydrogen atom or a $C_1$-$C_4$ alkyl group; and M⁻ represents the counterion of the corresponding organic acid, mineral acid or halide, d) one optionally cationic 5- or 6-membered heteroaryl radical, preferably imidazolium, optionally substituted with a ($C_1$-$C_4$)alkyl radical, preferably methyl; xi) acylamino (—N(R)—C(O)—R') in which the R radical is a hydrogen atom or a $C_1$-$C_4$ alkyl radical optionally bearing at least one hydroxyl group and the R' radical is a $C_1$-$C_2$ alkyl radical; xii) carbamoyl ((R)$_2$N—C(O)—) in which the R radicals, which may be identical or different, represent a hydrogen atom or a $C_1$-$C_4$ alkyl radical optionally bearing at least one hydroxyl group; xiii) alkylsulfonylamino (R'S(O)$_2$—N(R)—) in which the R radical represents a hydrogen atom or a $C_1$-$C_4$ alkyl radical optionally bearing at least one hydroxyl group and the R' radical represents a $C_1$-$C_4$ alkyl radical, a phenyl radical; xiv) aminosulfonyl ((R)$_2$N—S(O)$_2$—) in which the R radicals, which may be identical or different, represent a hydrogen atom or a $C_1$-$C_4$ alkyl radical optionally bearing at least one hydroxyl group; xv) carboxyl in the acid or salified form (preferably salified with an alkali metal or a substituted or unsubstituted ammonium); xvi) cyano; xvii) nitro; xviii) polyhaloalkyl, preferably trifluoromethyl; xix) a glycosylcarbonyl; xx) a phenylcarbonyloxy group optionally substituted with one or more hydroxyl groups; xxi) a glycosyloxy group; and xxii) a phenyl group optionally substituted with one or more hydroxyl groups;

for the purposes of the present invention, the term "glycosyl" radical means a radical derived from a mono- or polysaccharide;

the radicals "containing one or more silicon atoms" are preferably polydimethylsiloxane, polydiphenylsiloxane, polydimethylphenylsiloxane or stearoxy dimethicone radicals;

the "heterocyclic" radicals are radicals comprising, in at least one ring, one or more heteroatoms chosen in particular from O, N and S, preferably O or N, optionally substituted in particular with one or more alkyl, alkoxy, carboxyl, hydroxyl, amine or ketone groups. These rings may comprise one or more oxo groups on the carbon atoms of the heterocycle; mention may in particular be made, among the heterocyclic radicals that may be used, of furyl, pyranyl, pyrrolyl, imidazolyl, pyrazolyl, pyridyl or thienyl groups; even more preferably, the heterocyclic groups are fused groups, such as benzofuryl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, in particular with one or more OH groups.

The ODP(s) that are useful in the process of the invention may be natural or synthetic. Among the natural ODPs are compounds that may be present in nature and that are reproduced by chemical (semi)synthesis.

The salts of the ODPs of the invention may be salts of acids or of bases. The acids may be mineral or organic. Preferably, the acid is hydrochloric acid, which results in chlorides.

The term "basifying agents" means that the bases as defined for e) may be mineral or organic. In particular, the bases are alkali metal hydroxides, such as sodium hydroxide, which results in sodium salts.

According to a particular embodiment of the invention, the composition comprises, as ingredient a), one or more synthetic ODPs that do not exist in nature.

According to another preferred embodiment of the invention, the composition that is useful in the process for dyeing keratin fibres comprises, as ingredient a), one or more natural ODPs.

More particularly, the ODP(s) that may be used in the process of the invention according to a) are in particular:
flavanols, for instance catechin and epicatechin gallate,
flavonols, for instance quercetin,
anthocyanidins, for instance cyanidin, delphinidin and petunidin,
anthocyanins or anthocyans, for instance myrtillin,
ortho-hydroxybenzoates, for example gallic acid salts,
flavones, for instance luteolin,
hydroxystilbenes, for example 3,3',4,5'-tetrahydroxystilbene, optionally oxylated (for example glucosylated),
3,4-dihydroxyphenylalanine and derivatives thereof,
2,3-dihydroxyphenylalanine and derivatives thereof,
4,5-dihydroxyphenylalanine and derivatives thereof,
dihydroxycinnamates, such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
quinones,
hydroxyxanthones,
1,2-dihydroxybenzene and derivatives thereof,
1,2,4-trihydroxybenzene and derivatives thereof,
1,2,3-trihydroxybenzene and derivatives thereof,
2,4,5-trihydroxytoluene and derivatives thereof,
proanthocyanidins and especially the proanthocyanidins A1, A2, B1, B2, B3 and C1,
chroman and chromene compounds,
proathocyanins,
tannic acid,
ellagic acid,
and mixtures of the preceding compounds.

According to the invention, the term "chromene or chroman" ODP compounds means ODPs which comprise, in their structure, at least one bicycle of formula (A) below:

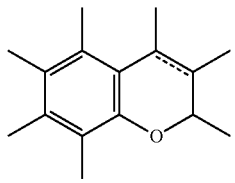

(A)

the endocyclic bond ---- representing a carbon-carbon single bond or else a carbon-carbon double bond, as illustrated by formula (A1) below, denoting the chromene family, and formula (A2) below, denoting the chroman family:

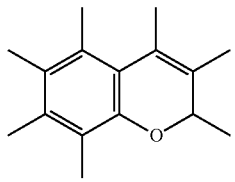

(A1)

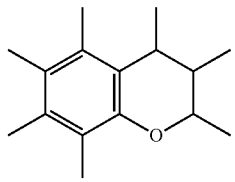

(A2)

More particularly, the ODPs of the invention are of formula (A) and are preferably chosen from the dyes of the following formulae:
formula (III), comprising, in its structure, the bicycle of formula (A2):

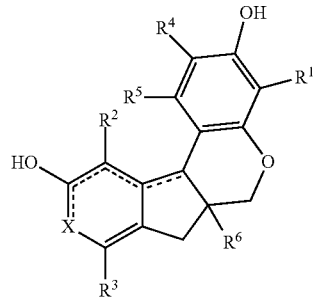

(III)

and also the tautomeric and/or mesomeric forms thereof, the stereoisomers thereof, the addition salts thereof with a cosmetically acceptable acid or base, and the hydrates thereof;
in which formula (III):
- ---- represents a carbon-carbon single bond or a carbon-carbon double bond, the sequence of these ---- bonds denoting two carbon-carbon single bonds and two carbon-carbon double bonds, said bonds being conjugated,
- X represents a group:

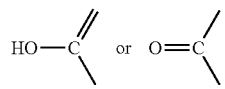

- $R^1$, $R^2$, $R^3$, $R^4$, $R^5$ and $R^6$, which may be identical or different, represent a hydrogen atom, a hydroxyl group, an optionally substituted alkyl group, an optionally substituted alkoxy group or an optionally substituted acyloxy group; and formula (IV), comprising, in its structure, the bicycle of formula (A1):

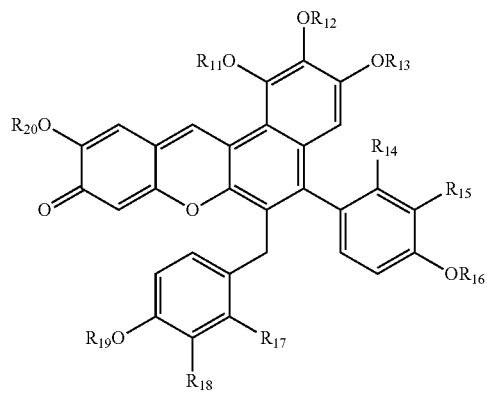

(IV)

and also the tautomeric and/or mesomeric forms thereof, the stereoisomers thereof, the addition salts thereof with a cosmetically acceptable acid or base, and the hydrates thereof;

in which formula (IV):

$R_{11}$, $R_{12}$, $R_{13}$, $R_{16}$, $R_{19}$ and $R_{20}$, which may be identical or different, represent a hydrogen atom or a $C_1$-$C_4$ alkyl radical, and $R_{14}$, $R_{15}$, $R_{17}$ and $R_{18}$, which may be identical or different, represent a hydrogen atom, a hydroxyl radical or a $C_1$-$C_4$ alkoxy radical.

As regards the ortho-diphenols of formula (III) as defined above, they may be found in two tautomeric forms denoted (IIIa) and (IIIb):

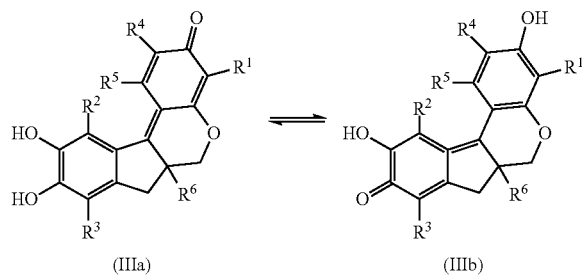

(IIIa)          (IIIb)

The alkyl radicals mentioned in the preceding definitions of the substituents are saturated and linear or branched hydrocarbon-based radicals, generally $C_1$-$C_{20}$, particularly $C_1$-$C_{10}$, preferably $C_1$-$C_6$, hydrocarbon-based radicals, such as methyl, ethyl, propyl, butyl, pentyl and hexyl.

The alkoxy radicals are alkyl-oxy radicals with the alkyl radicals as defined above and preferably the alkoxy radicals are $C_1$-$C_{10}$ alkoxy radicals, such as methoxy, ethoxy, propoxy and butoxy.

The alkyl or alkoxy radicals, when they are substituted, may be substituted with at least one substituent borne by at least one carbon atom chosen from: i) a halogen atom or ii) a hydroxyl group; iii) a $C_1$-$C_2$ alkoxy group; iv) a $C_1$-$C_{10}$ alkoxycarbonyl group; v) a (poly)hydroxy($C_2$-$C_4$)alkoxy group; vi) an amino group; vii) a 5- or 6-membered heterocycloalkyl group; viii) an optionally cationic 5- or 6-membered heteroaryl group, preferably imidazolium, optionally substituted with a ($C_1$-$C_4$)alkyl radical, preferably methyl; ix) an amino radical substituted with one or two identical or different $C_1$-$C_6$ alkyl radicals optionally bearing at least: a) one hydroxyl group,
b) one amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom, c) one quaternary ammonium group —N⁺R'R''R''', M⁻ for which R'', R'' and R''', which may be identical or different, represent a hydrogen atom or a $C_1$-$C_4$ alkyl group and M⁻ represents the counterion of the corresponding organic acid, mineral acid or halide, d) or one optionally cationic 5- or 6-membered heteroaryl radical, preferably imidazolium, optionally substituted with a ($C_1$-$C_4$)alkyl radical, preferably methyl; x) an acylamino (—NR—COR') radical in which the R radical is a hydrogen atom or a $C_1$-$C_4$ alkyl radical optionally bearing at least one hydroxyl group and the R' radical is a $C_1$-$C_2$ alkyl radical; xi) a carbamoyl (($R)_2$N—CO—) radical in which the R radicals, which may be identical or different, represent a hydrogen atom or a $C_1$-$C_4$ alkyl radical optionally bearing at least one hydroxyl group; xii) an alkylsulfonylamino ($R'SO_2$—NR—) radical in which the R radical represents a hydrogen atom or a $C_1$-$C_4$ alkyl radical optionally bearing at least one hydroxyl group and the R' radical represents a $C_1$-$C_4$ alkyl radical, a phenyl radical; xiii) an aminosulfonyl (($R)_2$N—$SO_2$—) radical in which the R radicals, which may be identical or different, represent a hydrogen atom or a $C_1$-$C_4$ alkyl radical optionally bearing at least one hydroxyl group; xiv) a carboxyl radical in the acid or salified form (preferably salified with an alkali metal or a substituted or unsubstituted ammonium); xv) a cyano group; xvi) a nitro group; xvii) a carboxyl or glycosylcarbonyl group; xviii) a phenylcarbonyloxy group optionally substituted with one or more hydroxyl groups; xix) a glycosyloxy group; and xx) a phenyl group optionally substituted with one or more hydroxyl groups.

The term "glycosyl radical" means a radical derived from a monosaccharide or polysaccharide.

Preferably, the alkyl or alkoxy radicals of formula (III) are unsubstituted.

According to a particular embodiment of the invention, the dyes of formula (III) comprise a radical $R_6$ representing a hydroxyl group.

Another particular embodiment of the invention relates to the ODPs of formula (III) for which the radical $R_1$ represents a hydrogen atom or a hydroxyl group.

More particularly, the composition according to the invention may comprise one or more ODPs of formula (III) chosen from haematoxylin, haematein, brazilin and brazilein.

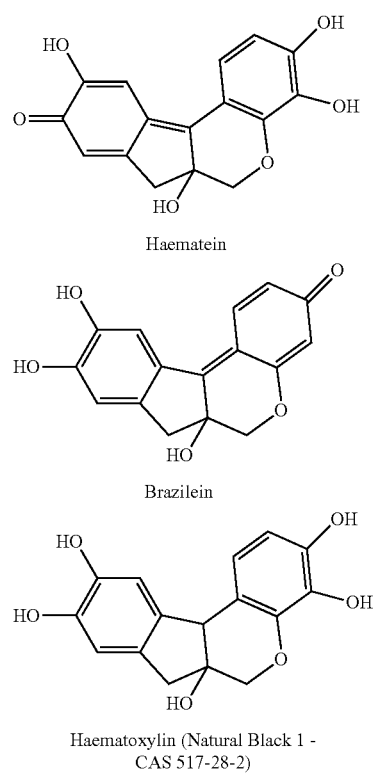

Haematein

Brazilein

Haematoxylin (Natural Black 1 - CAS 517-28-2)

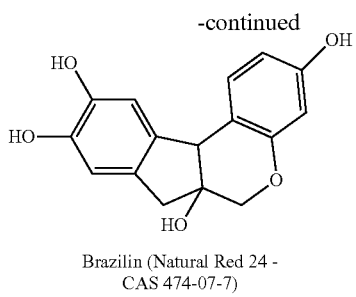

Brazilin (Natural Red 24 - CAS 474-07-7)

Brazilein is a conjugated form of a chroman compound of formula (A2). The tautomeric structures (IIIa) and (IIIb) illustrated above are found in the scheme below.

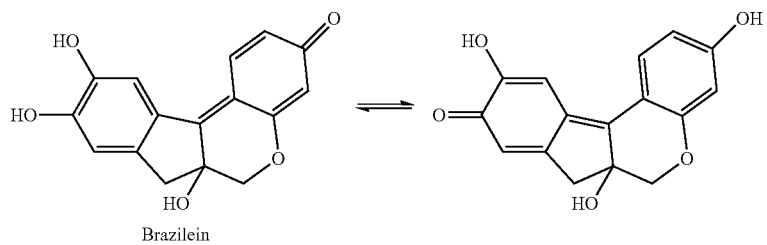 [SMILES: O=C1C=CC2=C3c4cc(O)c(O)cc4CC3(O)COC2=C1 ; O=C1C=C2CC3(O)COc4cc(O)ccc4C3=C2C=C1O]

Brazilein

Among the ODPs of haematoxylin/haematein and brazilin/brazilein type, examples that may be mentioned include haematoxylin (Natural Black 1 according to the INCI name) and brazilin (Natural Red 24 according to the INCI name), dyes of the indochroman family, which are commercially available. The latter dyes may exist in an oxidized form and may be obtained synthetically or by extraction of plants or vegetables known to be rich in these dyes.

The ODPs of formula (III) may be used in the form of extracts. Use may be made of the following plant extracts (genus and species): *Haematoxylon campechianum, Haematoxylon brasiletto, Caesalpinia echinata, Caesalpinia sappan, Caesalpinia spinosa* and *Caesalpinia brasiliensis*.

The extracts are obtained by extracting the various plant parts, for instance the root, the wood, the bark or the leaves.

According to one particular embodiment of the invention, the natural ODPs are of formula (I) and are obtained from logwood, pernambuco wood, *sappan* wood and Brazil wood.

According to a particular embodiment of the invention, the ODPs are of formula (IV), preferably those for which $R_{11}$ and $R_{13}$ represent an alkyl radical, preferably methyl.

Preferably, $R_{12}$, $R_{16}$, $R_{19}$ and $R_{20}$ denote, independently of each other, a hydrogen atom or an alkyl radical, preferably methyl.

Preferably, $R_{14}$ and $R_{17}$ denote, independently of each other, a hydrogen atom or an alkoxy radical, preferably methoxy.

Preferably, $R_{18}$ and $R_{15}$ denote, independently of each other, a hydrogen atom, a hydroxyl radical or an alkoxy radical, preferably methoxy.

A first particularly preferred family of ODPs that are suitable for use in the present invention is that of the dyes corresponding to formula (II) above for which $R_{12}$, $R_{15}$, $R_{16}$, $R_{17}$, $R_{19}$ and $R_{20}$ each represent a hydrogen atom. $R_{11}$ and $R_{13}$ each represent a methyl radical and $R_{14}$ represents a methoxy radical.

The preferred ODPs of this first family include those for which $R_{18}$ represents a methoxy radical (santalin B) or a hydroxyl radical (santalin A).

A second particularly preferred family of ODPs that are suitable for use in the present invention is that of the dyes corresponding to the formula (IV) above for which:
$R_{11}$ and $R_{13}$ each represent a methyl radical,
$R_{17}$ represents a methoxy radical.

A preferred dye of this second family is that for which, in addition, $R_{19}$ represents a methyl radical, $R_{20}$, $R_{12}$, $R_{14}$, $R_{18}$ and $R_{16}$ each represent a hydrogen atom and $R_{15}$ represents a hydroxyl radical (santarubin A).

A second preferred dye of this second family is that for which $R_{18}$, $R_{20}$, $R_{12}$, $R_{14}$ and $R_{16}$ represent a hydrogen atom, $R_{15}$ represents a methoxy radical and $R_{19}$ represent a methyl radical (santarubin B).

A third preferred family of ODPs of this second family is that for which $R_{20}$, $R_{12}$, $R_{14}$, $R_{15}$, $R_{16}$ and $R_{19}$ represent hydrogen and $R_{18}$ represents a hydroxyl radical (santarubin C).

The preferred ODP(s) of this second family is that for which $R_{15}$ represents a methoxy radical, $R_{18}$ and $R_{14}$ represent a hydrogen atom and $R_{20}$, $R_{12}$, $R_{16}$ and $R_{19}$ represent a methyl radical (tetra-O-methylsantarubin).

The ODP(s) of formula (IV) may be used in the form of extracts. Use may be made of plant extracts of red woods, bringing together generally the species of red woods from Asia and West Africa of the genus *Pterocarpus* and of the genus *Baphia*. These woods are, for example, *Pterocarpus santalinus, Pterocarpus osun, Pterocarpus soyauxii, Pterocarpus erinaceus, Pterocarpus indicus* or *Baphia nitida*. These woods may also be called padauk, sandalwood, narra wood, camwood or bar wood.

Thus, extracts that may be used, comprising ODPs of formula (II), in the present invention may be obtained, for example, from red sandalwood (*Pterocarpus santalinus*) by aqueous basic extraction, such as the product sold under the trade name Santal Concentre SL 709C by the company COPIAA, or also by means of solvent extraction of sandalwood powder, such as the product sold under the trade name Santal Poudre SL PP by the same company COPIAA. Mention may also be made of the aqueous/alcoholic extract of powdered red sandalwood from the company Alban Muller.

Extracts also suitable for the present invention can be obtained from woods such as camwood (*Baphia nitida*) or also bar wood (*Pterocarpus soyauxii, Pterocarpus erinaceus*): the latter is thus split up and then ground: a conventional alcoholic extraction or one by percolation is subsequently carried out on this ground material in order to collect a pulverulent extract particularly suitable for the implementation of the present invention.

The ODP salts of formulae (III) and (IV) of the invention may be salts of acids or bases that are cosmetically acceptable.

The acids may be mineral or organic. Preferably, the acid is hydrochloric acid, which results in chlorides.

The bases may be mineral or organic. In particular, the bases are alkali metal hydroxides such as sodium hydroxide which leads to sodium salts.

Preferably, the ODP(s) of formulae (III) and (IV) included in the composition according to the invention result from plant extracts. Use may also be made of mixtures of plant extracts.

The natural extracts of ODPs according to the invention may be in the form of powders or liquids. Preferably, the extracts are in powder form.

In particular, the ODPs of the invention are included among catechin, quercetin, brazilin, haematein, haematoxylin, chlorogenic acid, caffeic acid, gallic acid, catechol, L-DOPA, pelargonidin, cyanidin, (−)-epicatechin, (−)-epigallocatechin, (−)-epigallocatechin 3-gallate (EGCG), (+)-catechin, isoquercetin, pomiferin, esculetin, 6,7-dihydroxy-3-(3-hydroxy-2,4-dimethoxyphenyl)coumarin, santalin AC, mangiferin, butein, maritimetin, sulfuretin, robtein, betanidin, pericampylinone A, theaflavin, proanthocyanidin A2, proanthocyanidin B2, proanthocyanidin C1, procyanidins DP 4-8, tannic acid, purpurogallin, 5,6-dihydroxy-2-methyl-1,4-naphthoquinone, alizarin, wedelolactone, variegatic acid, gomphidic acid, xerocomic acid and carnosol, and natural extracts containing them.

Preferably, the ODPs of the invention are chromenes or chromans and are chosen from haematein, haematoxylin, brazilein, brazilin and santalin A.

The term "carboxylate" means carboxylic acid salt.

When the dye precursors have D and L forms, the two forms may be used in the compositions according to the invention, as may the racemic mixtures.

According to one embodiment, the natural ODPs are derived from extracts of animals, bacteria, fungi, algae, plants and fruits, used in their entirety or partially. In particular regarding plants, the extracts are derived from fruit, including citrus fruit, from vegetables, from trees and from shrubs. Use may also be made of mixtures of these extracts, which are rich in ODPs as defined above.

Preferably, the natural ODP(s) of the invention are derived from extracts of plants or plant parts.

For the purposes of the invention, these extracts will be placed in the same category as compounds a).

The extracts are obtained by extraction of various plant parts, for instance the root, the wood, the bark, the leaf, the flower, the fruit, the seed, the pod or the peel.

Among the plant extracts, mention may be made of extracts of tea leaves and of rose.

Among the fruit extracts, mention may be made of extracts of apple, of grape (in particular of grape seed) or extracts of cocoa beans and/or pods.

Among the vegetable extracts, mention may be made of extracts of potato or of onion peel.

Among the extracts of tree wood, mention may be made of extracts of pine bark and extracts of logwood.

Use may also be made of mixtures of plant extracts.

According to a particular embodiment of the invention, the ortho-diphenol derivative(s) are natural extracts, rich in ODPs.

According to a preferred embodiment, the dye(s) of the invention are solely natural extracts.

Preferentially, the dye(s) according to the invention are chosen from catechin, quercetin, haematein, haematoxylin, brazilein, brazilin, gallic acid and tannic acid, and natural extracts containing them chosen from grape marc, pine bark, green tea, onion, cocoa bean, logwood, red wood and gall nut.

More preferentially, the ODP(s) of the invention are chosen from:
haematein, brazilein, gallic acid or tannic acid, when the dyeing process does not use a chemical oxidizing agent;
or else
haematoxylin, brazilin, gallic acid or tannic acid, when the dyeing process uses a chemical oxidizing agent.

The natural extracts according to the invention may be in the form of powders or liquids. Preferably, the extracts of the invention are provided in the form of powders.

According to the invention, the synthetic or natural dye(s) and/or the natural extract(s) used as ingredient a) in one or more cosmetic compositions that are useful in the process according to the invention preferably represent from 0.001% to 20% by weight of the total weight of the composition(s) containing them.

As regards the pure dyes, especially the pure ODPs, the content in the composition(s) containing them is preferably between 0.001% and 5% by weight of each of these compositions containing them.

As regards the extracts, the content in the composition(s) containing the extracts per se is preferably between 0.1% and 20% by weight of each of these compositions, and better still between 0.5% and 10% by weight of the compositions containing them.

b) Titanium Salt(s):

The titanium salt(s) of the invention may be one or more organic or mineral titanium salts.

For the purposes of the present invention, the term "organic titanium salt" means the salts per se resulting from the action of at least one organic acid on Ti.

The term "organic acid" means an acid, i.e. a compound that is capable of releasing a cation or proton $H^+$ or $H_3O^+$, in aqueous medium, which comprises at least one optionally unsaturated, linear or branched $C_1$-$C_{20}$ hydrocarbon-based chain, or a (hetero)cycloalkyl or (hetero)aryl group and at least one acid chemical function chosen in particular from carboxyl COOH, sulfuric $SO_3H$, $SO_2H$, and phosphoric $PO_3H_2$, $PO_4H_2$. In particular, the organic acid(s) for forming the organic titanium salt(s) of the invention are chosen from the carboxylic acid(s) of formula (I) as defined previously and are preferably α-hydroxy acids such as lactic acid, glycolic acid, tartaric acid or citric acid.

Preferentially, the organic titanium salt derived from the action of one or more organic acids as defined previously, preferably carboxylic acids of formula (I) as defined previously, is an optionally charged (in particular negatively charged) complex, which is complexed with one or more carboxylate groups of carboxylic acids.

Preferentially, the organic titanium salt(s) of the invention are chosen from those of formula (I-A) below:

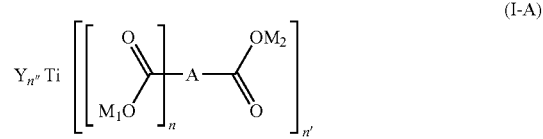

(I-A)

in which formula (I-A):
- A is identical to that of formula (I);
- n, n' and n", which may be identical or different, are equal to 1, 2, 3 or 4 and n'+n"=6;
- $M_1$ and $M_2$, which may be identical or different, represent a cationic counterion chosen in particular from cations of an alkali metal such as Na or K or of an alkaline-earth metal such as Ca or an organic cation such as ammonium, preferably ammonium or a hydrogen atom;
- $TiY_{n''}$ denoting $Ti(OH)_{n''}$, or $Ti(O)_{n''/2}$, or $Ti(OH)_{m1}(O)_{m2}$ with $m_1+m_2=n''$.

Preferentially, the radical A of compound (I-A) as defined previously represents a monovalent $(C_1-C_6)$alkyl or polyvalent $(C_1-C_6)$alkylene group optionally substituted with one or more hydroxyl groups, and n representing an integer between 0 and 5, such as between 0 and 2, inclusive; in particular, the carboxylic acid(s) used to form the organic titanium salt(s) of the invention are chosen from α-hydroxy acids; preferably, the acid is chosen from citric acid, lactic acid, tartaric acid and glycolic acid, better still from lactic acid and glycolic acid.

Preferentially, the organic titanium salt(s) of the invention are chosen from those of formula (I-B) below:

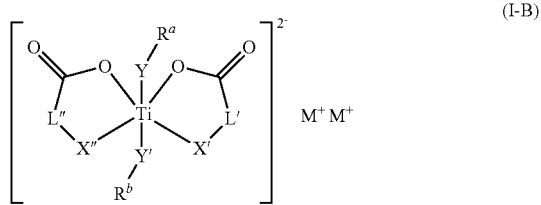

in which formula (I-B):
- L' and L", which may be identical or different, represent a divalent (hetero)arylene, $(C_1-C_6)$alkylene or $(C_2-C_6)$alkenylene group, said alkylene and arylene groups being optionally substituted with one or more atoms or groups chosen from halo, $(C_1-C_4)$alkyl, hydroxyl, thiol and $(di)(C_1-C_4)(alkyl)$amino, carboxyl, and/or optionally interrupted with one or more heteroatoms such as oxygen;
preferably, L' and L" are identical and represent a methylene or ethylene group optionally substituted with a $(C_1-C_4)$alkyl group;
- X' and X", which may be identical or different, represent a heteroatom such as oxygen, sulfur or amino $R^c$—N with $R^c$ representing a hydrogen atom or a $(C_1-C_4)$alkyl group; preferably, X' and X" are identical and represent an oxygen atom;
- Y and Y', which may be identical or different, are as defined for X' and X"; preferably, Y and Y' are identical and represent an oxygen atom;
- $R^a$ and $R^b$, which may be identical or different, represent a hydrogen atom or a $(C_1-C_6)$alkyl, $(C_2-C_6)$alkenyl or (hetero)aryl group; particularly, $R^a$ and $R^b$, which are identical, represent a hydrogen atom or a $(C_1-C_4)$alkyl group, preferably hydrogen;
- $M^+$, which may be identical or different, represents a cationic counterion such as a cation of an alkali metal (Na or K) or of an alkaline-earth metal (Ca) or an organic cation such as ammonium, preferably ammonium.

Preferably, the organic titanium salt(s) of the dyeing process are dihydroxybis(lactato)titanium(IV) salts such as those having the following formula:

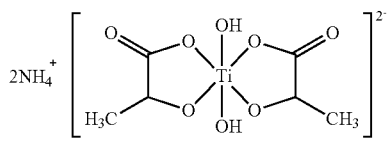

The dyeing process may use one or more organic acids b1) of formula (I) as defined previously.

According to an advantageous variant, the dyeing process also uses b1) one or more carboxylic acids of formula (I) as defined previously. More preferentially, the carboxylic acid(s) b1) are other than the carboxylic acids complexed to the Ti salts.

For example, if the carboxylic acid complexed to the titanium salt b) is lactic acid or the carboxylate salt thereof (lactate), the second acid b1) is other than lactic acid or lactate, and may be, for example, glycolic acid.

For the purposes of the present invention, the term "mineral titanium salt" means the salts per se derived from the action of a mineral acid on Ti.

The term "mineral acid" means an acid which does not comprise carbon atoms, apart from carbonic acid.

The mineral titanium salts are preferably chosen from titanium halides, titanium sulfates and titanium phosphates. Preferably, the titanium salts are mineral Ti(II), Ti(III) or Ti(IV) salts, more particularly Ti(III) or Ti(IV).

Preferably, the titanium salt(s) are organic titanium salts, and better still organic Ti(IV) salts. According to an advantageous embodiment of the invention, the organic Ti salt consists of a Ti(IV) atom and of 2 to 3 molar equivalents of at least one carboxylic acid of formula (I).

The titanium salt(s) (b) are present in the cosmetic composition(s) used in the process according to the invention in a content ranging from 0.001% to 20% by weight, relative to the total weight of the composition(s) containing them.

Particularly, the organic titanium salt(s) and the mineral titanium salt(s) according to the invention are soluble in water in a proportion of at least 0.0001 g/l and better still at least 1 g/l.

c) Cellulose-Based Polysaccharide(s)

In accordance with the present invention, the dyeing process uses c) one or more cellulose-based polysaccharides, i.e. one or more cellulose-based polysaccharide polymers, which are preferably thickeners.

The cellulose-based polymers may be associative or non-associative anionic, cationic, amphoteric or nonionic polymers.

According to the invention, the term "cellulose-based polysaccharide" means any polymer bearing in its structure sequences of glucose residues linked via β-1,4 bonds; besides unsubstituted celluloses, the cellulose derivatives may be anionic, cationic, amphoteric or nonionic. Thus, the cellulose-based polysaccharides of the invention may be chosen from unsubstituted celluloses, including those in a microcrystalline form, and cellulose ethers. Among these cellulose-based polysaccharides, cellulose ethers, cellulose esters and cellulose ester ethers are distinguished. Among the cellulose esters are mineral esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/mineral esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

The term "associative polymers" means polymers that are capable, in an aqueous medium, of reversibly combining with each other or with other molecules. Their chemical structure more particularly comprises at least one hydrophilic region and at least one hydrophobic region, preferably one or more hydrophobic hydrocarbon-based side chains.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms. Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene. According to a particular embodiment of the invention, the cellulose-based polysaccharide(s) are non-associative.

The "non-associative" cellulose-based polysaccharides of the invention are cellulose-based polysaccharides not comprising any fatty chains, i.e. preferably not comprising any $C_{10}$-$C_{30}$ chains in their structure.

According to a first variant, the non-associative cellulose-based polysaccharide(s) are nonionic. Mention may be made of nonionic cellulose ethers without a $C_{10}$-$C_{30}$ fatty chain, i.e. which are "non-associative", mention may be made of ($C_1$-$C_4$)alkylcelluloses, such as methylcelluloses and ethylcelluloses (for example, Ethocel standard 100 Premium from Dow Chemical); (poly)hydroxy($C_1$-$C_4$)alkylcelluloses, such as hydroxymethylcelluloses, hydroxyethylcelluloses (for example, Natrosol 250 HHR provided by Aqualon) and hydroxypropylcelluloses (for example, Klucel EF from Aqualon); mixed (poly)hydroxy($C_1$-$C_4$)alkyl($C_1$-$C_4$)alkylcelluloses, such as hydroxypropylmethylcelluloses (for example, Methocel E4M from Dow Chemical), hydroxyethylmethylcelluloses, hydroxyethylethylcelluloses (for example, Bermocoll E 481 FQ from Akzo Nobel) and hydroxybutylmethylcelluloses.

According to a second variant, the non-associative cellulose-based polysaccharide(s) are anionic. Among the anionic cellulose ethers without a fatty chain, mention may be made of (poly)carboxy($C_1$-$C_4$)alkylcelluloses and salts thereof. Examples that may be mentioned include carboxymethylcelluloses, carboxymethylmethylcelluloses (for example Blanose 7M from the company Aqualon) and carboxymethylhydroxyethylcelluloses, and the sodium salts thereof.

According to a third variant, the non-associative cellulose-based polysaccharide(s) are cationic. Among the cationic cellulose ethers without a fatty chain, mention may be made of cationic cellulose derivatives such as cellulose copolymers or cellulose derivatives grafted with a water-soluble quaternary ammonium monomer, and described in particular in U.S. Pat. No. 4,131,576, such as (poly)hydroxy ($C_1$-$C_4$)alkyl celluloses, for instance hydroxymethyl-, hydroxyethyl- or hydroxypropylcellu loses grafted especially with a methacryloylethyltrimethylammonium, methacrylamidopropyltrimethylammonium or dimethyldiallylammonium salt. The commercial products corresponding to this definition are more particularly the products sold under the names Celquat® L 200 and Celquat® H 100 by the company National Starch.

According to another particular embodiment of the invention, the cellulose-based polysaccharide(s) are associative.

Mention may be made especially of quaternized (poly) hydroxyethylcelluloses modified with groups comprising at least one fatty chain, such as alkyl, arylalkyl or alkylaryl groups comprising at least 8 carbon atoms, or mixtures thereof. The alkyl radicals borne by the above quaternized celluloses or hydroxyethylcelluloses preferably comprise from 8 to 30 carbon atoms. The aryl radicals preferably denote phenyl, benzyl, naphthyl or anthryl groups. Examples of quaternized alkylhydroxyethylcelluloses containing $C_8$-$C_{30}$ fatty chains that may be indicated include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Aqualon, and the products Crodacel QM®, Crodacel QL® ($C_{12}$ alkyl) and Crodacel QS® ($C_{18}$ alkyl) sold by the company Croda and the product Softcat SL 100® sold by the company Aqualon.

Mention may also be made of celluloses or derivatives thereof, modified with groups comprising at least one fatty chain, such as alkyl, arylalkyl or alkylaryl groups or mixtures thereof in which the alkyl groups are of $C_8$, and in particular:

nonionic alkylhydroxyethylcelluloses such as the products Natrosol Plus Grade 330 CS and Polysurf 67 ($C_{16}$ alkyl) sold by the company Aqualon;

nonionic nonoxynylhydroxyethylcelluloses such as the product Amercell HM-1500 sold by the company Amerchol;

nonionic alkylcelluloses such as the product Bermocoll EHM 100 sold by the company Berol Nobel.

Among the cellulose-based polysaccharides according to the invention, mention may be made of fatty-phase thickeners, especially polymers bearing in the backbone at least one crystallizable block. As cellulose-based polysaccharides, which are in particular fatty-phase thickeners, use may thus be made of semicrystalline cellulose-based polysaccharides. The semicrystalline cellulose-based polysaccharides that may be used in the context of the invention may be non-crosslinked or partially crosslinked, provided that the degree of crosslinking does not impede their dissolution or dispersion in the liquid oily phase by heating above their melting point. It may then be a case of chemical crosslinking, by reaction with a multifunctional monomer during the polymerization. It may also be a case of physical crosslinking, which may then be due either to the establishment of bonds of hydrogen or dipolar type between groups borne by the polysaccharide, for instance dipolar interactions between carboxylate ionomers, these interactions being in small amount and borne by the polymer backbone; or due to a phase separation between the crystallizable blocks and the amorphous blocks borne by the polysaccharide.

Preferably, the semicrystalline cellulose-based polysaccharides that are suitable for use in the invention are non-crosslinked.

According to a particular embodiment of the invention, the cellulose-based polysaccharide(s) are especially mono-alkyl or polyalkyl esters of cellulose and of fatty acids, especially corresponding to formula (C1) below:

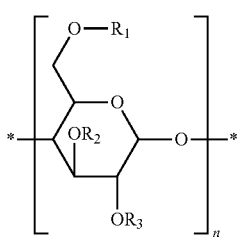

(C1)

in which formula (C1):

n is an integer ranging from 3 to 200, especially ranging from 20 to 150 and in particular ranging from 25 to 50, $R_1$, $R_2$ and $R_3$, which may be identical or different, are chosen from hydrogen and an acyl group (R—C(O)—) in which the radical R is a linear or branched, saturated or unsaturated hydrocarbon-based group containing from 7 to 29, in particular from 7 to 21, especially from 11 to 19, more particularly from 13 to 17, or even 15, carbon atoms, with the proviso that at least one of said radicals $R_1$, $R_2$ or $R_3$ is other than hydrogen.

In particular, $R_1$, $R_2$ and $R_3$ may represent hydrogen or an acyl group (R—C(O)—) in which R is a hydrocarbon-based radical as defined above, with the proviso that at least two of said radicals $R_1$, $R_2$ and $R_3$ are identical and other than hydrogen.

The radicals $R_1$, $R_2$ and $R_3$ may all contain an acyl group (R—C(O)), which is identical or different and especially identical.

In particular, n mentioned previously advantageously ranges from 25 to 50 and is especially equal to 38 in the general formula of the saccharide ester that may be used in the present invention.

In particular, when the radicals $R_1$, $R_2$ and/or $R_3$, which may be identical or different, contain an acyl group (R—C(O)), these radicals may be chosen especially from caprylic, capric, lauric, myristic, palmitic, stearic, arachic, behenic, isobutyric, isovaleric, 2-ethylbutyric, ethylmethylacetic, iso-heptanoic, 2-ethylhexanoic, isononanoic, isodecanoic, isotridecanoic, isomyristic, isopalmitic, isostearic, isoarachic, isohexanoic, decenoic, dodecenoic, tetradecenoic, myristoleic, hexadecenoic, palmitoleic, oleic, elaidic, asclepinic, gondoleic, eicosenoic, sorbic, linoleic, linolenic, punicic, stearidonic, arachidonic and stearolic radicals, and mixtures thereof.

The cellulose-based polysaccharides, which are in particular thickeners, may be used alone or as mixtures in all proportions. Preferably, the thickeners are aqueous-phase thickeners.

Preferably, the cellulose-based polysaccharides in accordance with the present invention advantageously have in solution or in dispersion, at 1% active material in water, a viscosity, measured using a rheometer at 25° C., of greater than 0.1 ps and even more advantageously greater than 0.2 cp, at a shear rate of 200 $s^{-1}$.

Preferably, the cellulose-based polysaccharide(s) c) of the invention are chosen from cellulose ethers, in particular hydroxyalkylcelluloses, in particular hydroxy($C_1$-$C_4$)alkylcelluloses, and especially chosen from hydroxymethylcelluloses, hydroxyethylcelluloses and hydroxypropylcelluloses.

The hydroxyalkylcelluloses may be nonionic, cationic and anionic. They are preferably nonionic. The hydroxyalkylcelluloses of the invention are preferably hydroxyethylcelluloses and more preferentially nonionic hydroxyethylcelluloses.

Use will be made even more preferentially of nonionic hydroxyethylcelluloses free of fatty chains or of cetylhydroxyethylcelluloses, for instance the compounds sold under the names Polysurf 67CS®, Natrosol 250MR®, Natrosol 250HHR® and Natrosol Plus 330® by the company Ashland, and mixtures thereof.

The cellulose-based polysaccharide(s) of the invention may be present in the dye composition(s) of the invention in contents ranging from 0.01% to 30% by weight, in particular from 0.05% to 20% by weight and better still from 0.1% to 10% by weight, relative to the total weight of the composition containing them.

d) Liquid Organic Compound(s) with a Value $\delta H<16$ $(MPa)^{1/2}$

According to a particular preferred embodiment of the invention, the dyeing process also uses d) one or more liquid organic compounds which have a Hansen solubility parameter value $\delta H$ of less than 16 $(MPa)^{1/2}$ at 25° C. and preferably less than or equal to 15 $(MPa)^{1/2}$.

It is understood that the liquid organic compound(s) with a Hansen solubility parameter value $\delta H$ of less than 16 $(MPa)^{1/2}$ at 25° C. d) are different from the carboxylic acid(s) b1) of formula (I) as defined previously. It is also understood that the organic compound(s) with a solubility parameter value $\delta H<16$ $(MPa)^{1/2}$ at 25° C. d) are soluble in water with a solubility of greater than 10 g/l of water at 25° C.

For the purposes of the present invention, the term "liquid organic compound" means an organic compound that is liquid at room temperature at 25° C.

The liquid organic compound(s) with a Hansen solubility parameter value $\delta H$ of less than 16 $(MPa)^{1/2}$ at 25° C. are described, for example, in the reference book *Hansen solubility parameters A user's handbook*, Charles M. Hansen, CRC Press, 2000, pages 167 to 185 and also in the book *Handbook of solubility parameters and other cohesion parameters CRC Press*, pages 95 to 121 and pages 177 to 185, *The 3 dimensional solubility parameter & solvent diffusion coefficient, their importance in surface coating formulation*, Charles M. Hansen, Copenhagen Danish Technical Press, 1967, pages 13-29.

As a reminder, the organic compounds have a global Hansen solubility parameter $\delta$, which is defined in the article "*Solubility parameter values*" by Eric A. Grulke in the "*Polymer Handbook*", 3rd Edition, Chapter VII, pages 519-559, by the relationship:

$$\delta=(\delta_d^2+\delta_p^2+\delta_h^2)^{1/2}$$

in which relationship:

$\delta_d$ characterizes the London dispersion forces derived from the formation of dipoles induced during molecular impacts, i.e. nonpolar interactions, $\delta_p$ characterizes the Debye interaction forces between permanent dipoles, $\delta_h$ characterizes the interaction forces of hydrogen bonding type.

Thus, the Hansen solubility parameter $\delta H$ takes into account the solubility associated with the formation of hydrogen bonds in the liquid organic compounds.

According to one embodiment, the liquid organic compound(s) have a Hansen solubility parameter value $\delta H$ ranging from 6 $(MPa)^{1/2}$ to 14 $(MPa)^{1/2}$ at 25° C., and preferably ranging from 4 $(MPa)^{1/2}$ to 10 $(MPa)^{1/2}$ at 25° C.

Preferably, the liquid organic compound(s) comprise a molecular weight of less than 500 g/mol and even more preferentially less than 250 g/mol.

Among the liquid organic compounds with a Hansen solubility parameter value δH of less than 16 and particularly less than or equal to 15 (MPa)$^{1/2}$ at 25° C., mention may be made of propylene glycol derivatives, phenyl alcohols such as benzyl alcohol, alkylene carbonates and lactones, in particular the lactones of formula (D1):

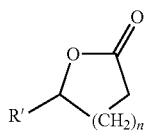

(D1)

in which formula (D1):
n is 1, 2 or 3;
R' represents a hydrogen atom; a linear or branched $C_1$-$C_8$ alkyl radical; a linear or branched $C_1$-$C_4$ hydroxyalkyl radical.

In accordance with an advantageous embodiment, the liquid organic compound(s) with a Hansen solubility parameter value δH of less than 16 (MPa)$^{1/2}$ at 25° C. are chosen from the following compounds:

| Name | δH |
|---|---|
| Benzyl alcohol | 13.7 |
| Dipropylene glycol methyl ether | 11.2 |
| Tripropylene glycol methyl ether | 10.4 |
| Propylene glycol n-butyl ether (PnB) | 9.2 |
| Propylene glycol n-propyl ether (PnP) | 9.2 |
| Dipropylene glycol monomethyl ether acetate | 8 |
| 3-Phenyl-1-propanol | 12.1 |
| 2-Phenyl-1-propanol | 12.9 |
| Ethylene glycol 2-ethylhexyl ether | 5.1 |
| 1-Octanol | 11.9 |
| 1-Decanol | 10 |
| Tridecyl alcohol | 9 |
| γ-Butyrolactone | 7.4 |
| Propylene carbonate | 4.1 |

Preferably, the liquid organic compound(s) with a Hansen solubility parameter value δH of less than 16 (MPa)$^{1/2}$ at 25° C. are chosen from alcohols, ethers and acids and/or a mixture of these compounds.

Preferably, the liquid organic compound(s) with a Hansen solubility parameter value δH of less than 16 (MPa)$^{1/2}$ at 25° C. are chosen from:
propylene glycol derivatives such as propylene glycol butyl ether, dipropylene glycol methyl ether, tripropylene glycol methyl ether or propylene glycol propyl ether, propylene glycol n-butyl ether, dipropylene glycol monomethyl ether acetate;
aromatic alcohols, preferably phenyl alcohols such as benzyl alcohol, 3-phenyl-1-propanol or 2-phenyl-1-ethanol;
alkylene carbonates;
lactones, in particular the lactones of formula (D1);
alcohols such as 1-Decanol or 1-Octanol;
ethers such as ethylene glycol 2-ethylhexyl ether;
and/or a mixture of these compounds.

Preferably, the liquid organic compound(s) with a Hansen solubility parameter value δH of less than 16 (MPa)$^{1/2}$ at 25° C. are chosen from alcohols, aromatic alcohols, in particular from benzyl alcohol, ethers, propylene glycol derivatives, and/or a mixture of these compounds.

According to one embodiment, the liquid organic compound(s) with a Hansen solubility parameter value δH of less than 16 (MPa)$^{1/2}$ at 25° C. are chosen from alcohols.

In particular, the alcohol(s) that may be used as liquid organic compounds with a Hansen solubility parameter δH as described above may be chosen from aromatic alcohols, in particular from benzyl alcohol, 3-phenyl-1-propanol and 2-phenyl-1-ethanol, and/or a mixture of these compounds.

According to one embodiment, the liquid organic compound(s) with a Hansen solubility parameter value δH of less than 16 (MPa)$^{1/2}$ at 25° C. are chosen from ethers.

In particular, the ethers that may be used as liquid organic compounds with a Hansen solubility parameter δH as described above may be propylene glycol butyl ether, dipropylene glycol methyl ether, tripropylene glycol methyl ether or propylene glycol propyl ether.

Preferably, the liquid organic compound(s) with a Hansen solubility parameter value δH of less than 16 (MPa)$^{1/2}$ at 25° C. are chosen from benzyl alcohol, preferably benzyl alcohol.

The liquid organic compound(s) with a Hansen solubility parameter δH of less than 16 (MPa)$^{1/2}$ at 25° C. may be present in the composition containing them in a content of greater than or equal to 0.5% by weight, preferably in a content of greater than or equal to 1% by weight, more preferentially in a content ranging from 1% to 40% by weight and better still from 5% to 30% by weight relative to the total weight of the composition containing them.

e) Chemical Oxidizing Agent(s)

According to a particular embodiment of the invention, the dyeing process also uses one or more chemical oxidizing agents. The term "chemical oxidizing agent" means an oxidizing agent other than atmospheric oxygen. More particularly, the dyeing process uses i) hydrogen peroxide; ii) urea peroxide; iii) polymeric complexes that can release hydrogen peroxide, such as polyvinylpyrrolidone/$H_2O_2$, provided in particular in the form of powders, and the other polymeric complexes described in U.S. Pat. Nos. 5,008,093, 3,376,110 and 5,183,901; iv) oxidases in the presence of an appropriate substrate (for example, glucose in the case of glucose oxidase or uric acid with uricase); v) metal peroxides which generate hydrogen peroxide in water, such as calcium peroxide or magnesium peroxide; vi) perborates; and/or vii) percarbonates.

According to a preferred embodiment of the invention, the composition comprises one or more chemical oxidizing agents chosen from i) urea peroxide; ii) polymeric complexes which can release hydrogen peroxide chosen from polyvinylpyrrolidone/$H_2O_2$; iii) oxidases; iv) perborates and v) percarbonates.

In particular, the dyeing process uses hydrogen peroxide.

Moreover, the composition(s) comprising hydrogen peroxide or a hydrogen peroxide-generating system may also include various adjuvants conventionally used in compositions for dyeing keratin fibres as defined below.

According to a particular embodiment of the invention, the chemical oxidizing agent(s) used preferably represent from 0.001% to 12% by weight of chemical oxidizing agents (of hydrogen peroxide) relative to the total weight of the composition(s) containing it or them, and even more preferentially from 0.2% to 2.7% by weight.

f) Basifying Agent(s)

According to a particular embodiment of the invention, the dyeing process uses one or more basifying agents f). These are base(s) that can increase the pH of the composition(s) in which they are present. The basifying agent is a Brønsted, Lowry or Lewis base. It may be mineral or organic.

Particularly, said agent is chosen from i) (bi)carbonates, ii) aqueous ammonia, iii) alkanolamines such as monoethanolamine, diethanolamine, triethanolamine and derivatives thereof, iv) oxyethylenated and/or oxypropylenated ethylenediamines, v) mineral or organic hydroxides, vi) alkali metal silicates such as sodium metasilicate, vii) amino acids, preferably basic amino acids such as arginine, lysine, ornithine, citrulline and histidine, and viii) the compounds of formula (XIII) below:

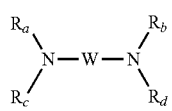

(XIII)

in which formula (XIII) W is a divalent $(C_1-C_8)$alkylene radical optionally substituted with at least one hydroxyl group or at least one $(C_1-C_4)$alkyl radical and/or optionally interrupted with at least one heteroatom, such as oxygen or sulfur, or with an —$N(R_e)$— group; $R_a$, $R_b$, $R_c$, $R_d$ and $R_e$, which may be identical or different, represent a hydrogen atom or a $(C_1-C_4)$alkyl or hydroxy$(C_1-C_4)$alkyl radical; preferably, W represents a propylene radical. The mineral or organic hydroxides are preferably chosen from a) hydroxides of an alkali metal, b) hydroxides of an alkaline-earth metal, for instance sodium hydroxide or potassium hydroxide, c) hydroxides of a transition metal, such as hydroxides of metals from groups III, IV, V and VI, d) hydroxides of lanthanides or actinides, quaternary ammonium hydroxides and guanidinium hydroxide.

The hydroxide may be formed in situ, for instance guanidine hydroxide, formed by reacting calcium hydroxide with guanidine carbonate.

The term "(bi)carbonates" i) is understood to mean:
 a) carbonates of alkali metals ($Met_2^+$, $CO_3^{2-}$), of alkaline-earth metals ($Met'^{2+}$, $CO_3^{2-}$) of ammonium (($R''_4N^+)_2$, $CO_3^{2-}$) or of phosphonium (($R''_4P^+)_2$, $CO_3^{2-}$ with Met' representing an alkaline-earth metal and Met representing an alkali metal, and R", which may be identical or different, represent a hydrogen atom or an optionally substituted $(C_1-C_6)$alkyl group such as hydroxyethyl); and
 b) bicarbonates, also known as hydrogen carbonates, of the following formulae:
  $R'^+$, $HCO_3^-$, with R' representing a hydrogen atom, an alkali metal, an ammonium group $R''_4N^+$— or a phosphonium group $R''_4P^+$—, where R", which may be identical or different, represent a hydrogen atom or an optionally substituted $(C_1-C_6)$alkyl group, such as hydroxyethyl, and, when R' represents a hydrogen atom, the hydrogen carbonate is then known as dihydrogen carbonate ($CO_2$, $H_2O$); and
  $Met'^{2+}$ $(HCO_3^-)_2$, with Met' representing an alkaline-earth metal.

More particularly, the basifying agent is chosen from alkali metal or alkaline-earth metal (bi)carbonates and amino acids such as arginine; preferentially alkali metal (bi)carbonates and amino acids.

Mention may be made of Na, K, Mg and Ca carbonates or hydrogen carbonates and mixtures thereof, and in particular sodium hydrogen carbonate. These hydrogen carbonates may originate from a natural water, for example spring water from the Vichy basin or from La Roche-Posay or Badoit water (cf. patent, for example the document FR 2 814 943). Mention may in particular be made of sodium carbonate [497-19-8]=$Na_2CO_3$, sodium hydrogen carbonate or sodium bicarbonate [144-55-8]=$NaHCO_3$, and sodium dihydrogen carbonate=$Na(HCO_3)_2$.

According to a particularly advantageous embodiment, the basifying agent(s) f) are chosen from amino acids, such as arginine, and (bi)carbonates, in particular alkali metal or alkaline-earth metal (bi)carbonates, alone or as mixtures. They are preferentially together during the dyeing process.

The basifying agent(s) as defined above preferably represent from 0.001% to 10% by weight of the weight of the composition(s) containing them, more particularly from 0.005% to 8% by weight of the composition.

Water:

According to one embodiment of the invention, water is preferably included in the process of the invention. It may originate from the moistening of the keratin fibres and/or from the composition(s) comprising compounds a) to e) as defined previously or from one or more other compositions.

Preferably, the water originates at least from a composition comprising at least one compound chosen from a) to f) as defined previously.

The Compositions:

The compositions according to the invention generally comprise water or a mixture of water and of one or more organic solvents or a mixture of organic solvents.

The term "organic solvent" means an organic substance that is capable of dissolving or dispersing another substance without chemically modifying it.

The compositions according to the invention may optionally comprise an organic solvent other than the liquid organic compound(s) which have a Hansen solubility parameter value δH of less than 16 $(MPa)^{1/2}$ at 25° C. d) as defined previously.

The Adjuvants:

The composition(s) of the dyeing process in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof other than the cellulose-based polysaccharides c) as defined previously, mineral or organic thickeners other than the cellulose-based polysaccharides c) as defined previously, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The dyeing process of the invention may also use, in addition to compounds a), b), optionally c) and optionally d), at least one other particular carboxylic acid of formula (I) as defined previously. More particularly, the carboxylic acid(s) of formula (I) are such that A represents a monovalent $(C_1-C_6)$alkyl or polyvalent $(C_1-C_6)$alkylene group optionally substituted with one or more hydroxyl groups, and n represents an integer between 0 and 5, such as between 0 and 2, inclusive.

More particularly, the carboxylic acid(s) of the invention are chosen from the acids of formula (I) having a solubility in water of greater than or equal to 1% by weight at 25° C. and at atmospheric pressure.

Preferably, the acids of formula (I) comprise at least one hydroxyl group in their structure. Even more preferentially, the acid is chosen from α-hydroxy acids. The preferred acids of the invention are chosen from glycolic acid, lactic acid, tartaric acid and citric acid.

The salts of the acids of formula (I) may be salts of organic or mineral bases, such as sodium hydroxide, aqueous ammonia or potassium hydroxide, or salts of organic amines, such as alkanolamines. The acids of formula (I) or salts thereof are present in the composition(s) containing them in a content ranging from 0.1% to 20% by weight.

Said adjuvants are preferably chosen from surfactants such as anionic or nonionic surfactants or mixtures thereof and mineral or organic thickeners.

The above adjuvants are generally present in an amount for each of them of between 0.01% and 40% by weight relative to the weight of the composition, and preferably between 0.1% and 20% by weight relative to the weight of the composition.

Needless to say, a person skilled in the art will take care to select this or these optional additional compound(s) such that the advantageous properties intrinsically associated with the composition(s) that are useful in the dyeing process in accordance with the invention are not, or are not substantially, adversely affected by the envisaged addition(s).

The cosmetic composition(s) of the invention may be in various galenical forms, such as a powder, a lotion, a mousse, a cream or a gel, or in any other form that is suitable for dyeing keratin fibres. They may also be packaged in a propellant-free pump-action bottle or under pressure in an aerosol container in the presence of a propellant and form a foam.

pH of the Composition(s):

According to a preferred embodiment of the invention, the pH of at least one of the cosmetic compositions comprising at least one of the ingredients a), b), c), d) and e) is acidic, i.e. less than 7.0, preferably less than 5.0, in particular at a pH of between 0 and 4 inclusive, more particularly between 0.5 and 3.5.

According to one embodiment, the pH of the cosmetic composition(s) comprising one or more alkaline agents preferably chosen from (bi)carbonates is alkaline, i.e. greater than 7, preferably of between 8 and 12 and more particularly of between 8 and 10.5 inclusive.

When the process according to the invention uses one or more ODP dyes, the composition containing the ODP(s) a) preferably has an acidic pH of less than 7, preferably less than 5, in particular a pH between 0 and 4 inclusive and better still between 1 and 3.

According to a particular embodiment of the invention, the composition containing the titanium salt(s) b) and not containing (bi)carbonates has a pH of less than 7 and preferably of less than 5, in particular a pH between 0 and 4 inclusive, more particularly between 0.5 and 3.5.

The pH of these compositions may be adjusted to the desired value by means of basifying agents as defined previously in f) or by using acidifying agents usually used in the dyeing of keratin fibres, or alternatively by means of standard buffer systems. Among the acidifying agents for the compositions used in the invention, examples that may be mentioned include mineral or organic acids, for instance hydrochloric acid, orthophosphoric acid, sulfuric acid, carboxylic acids, for instance acetic acid, tartaric acid, citric acid or lactic acid, or sulfonic acids.

The term "carboxylic acid" means a compound comprising at least one carboxylic acid —C(O)—OH group, preferably of formula (I) as defined previously, preferably comprising between 1 and 4 carboxylic acid groups, such as 1 or 2; or chosen from: i) $(C_1-C_{10})$alkyl-$[C(O)-OH]_n$ and ii) het-$[C(O)-OH]_n$, with n an integer between 1 and 4 inclusive, preferably between 1 and 2, het representing a heterocyclic group, such as pyrrolidone, it being possible for the alkyl or het group to be optionally substituted with one or more groups chosen especially from OH, and $(di)(C_1-C_6)$(alkyl)amino.

Dyeing Process in One or More Steps

The process for dyeing keratin fibres consists in treating, in one or more steps, with one or more cosmetic compositions containing the following ingredients, taken together or separately in said composition(s):

a) one or more dyes chosen from synthetic direct dyes and dyes of natural origin as defined previously, preferably chosen from the ODPs as defined previously;

b) one or more titanium salts; optionally b1) one or more carboxylic acids of formula (I) as defined previously;

c) one or more cellulose-based polysaccharides as defined previously;

d) optionally one or more liquid organic compounds which have a Hansen solubility parameter value δH of less than 16 $(MPa)^{1/2}$ at 25° C. and preferably less than or equal to 15 $(MPa)^{1/2}$;

e) optionally one or more chemical oxidizing agents chosen especially from hydrogen peroxide or one or more hydrogen peroxide-generating systems;

preferably, the composition or at least one of the compositions used in the dyeing process is at acidic pH, i.e. less than 7, preferably less than 5, in particular at a pH of between 0 and 4 inclusive.

According to a particular embodiment of the invention, the dyeing process is performed in at least two steps which comprise a first step in which the keratin fibres are treated with a cosmetic composition comprising a) one or more dyes chosen from synthetic direct dyes and dyes of natural origin, preferably one or more ODPs as defined previously, b) one or more titanium salts and optionally b1) one or more carboxylic acids as defined previously, c) one or more cellulose-based polysaccharides as defined previously, and d) optionally one or more liquid organic compounds with a Hansen solubility parameter value δH<16 $(MPa)^{1/2}$ at 25° C., preferably less than or equal to 15 $(MPa)^{1/2}$; followed by a second step in which an alkaline cosmetic composition, i.e. a composition whose pH is greater than 7, preferably between 8 and 12 and in particular between 8 and 10.5, which comprises e) one or more basifying agents and optionally f) one or more chemical oxidizing agents, is applied.

Preferentially, the composition comprising a)+b)+c)+optionally d) and optionally b1) and optionally e) is at acidic pH, i.e. less than 7, preferably less than 5, in particular at a pH of between 1 and 3 inclusive.

Preferentially, the cosmetic composition applied to the keratin fibres during the second step also comprises e) one or more chemical oxidizing agents chosen especially from hydrogen peroxide and one or more hydrogen peroxide-generating systems, preferably hydrogen peroxide.

The leave-on time after applying the composition comprising the dye(s), especially the ODP(s) as defined previously, is generally set at between 3 and 120 minutes, preferentially between 10 and 60 minutes and more preferentially between 15 and 45 minutes.

According to a particular embodiment of the invention, the process for dyeing keratin fibres is performed in two steps by applying to the keratin fibres a dye composition comprising ingredients a), b), b1), c) and optionally d) as defined previously and then, in a second step, a composition comprising ingredient e) and optionally ingredient f) as defined previously is applied to said keratin fibres, it being understood that at least one of the two compositions is aqueous. Preferably, the composition comprising the dye(s), especially the ODP(s) a) is aqueous. Even more preferentially, the two compositions used in this embodiment are aqueous.

According to a particular embodiment of the invention, the dyeing process is performed in several steps by applying to the keratin fibres, in a first step, a cosmetic composition comprising:
a) one or more ODPs as defined previously, especially chosen from:
haematein, brazilein, gallic acid or tannic acid, when the dyeing process does not use a chemical oxidizing agent e); or else
haematoxylin or brazilin, when the dyeing process uses a chemical oxidizing agent e);
b) one or more organic titanium salts as defined previously; advantageously, ingredient b) is chosen from Ti(IV) salts or complexes; b1) optionally one or more carboxylic acids of formula (I) as defined previously; and
c) one or more cellulose-based polysaccharide(s) as defined previously;
d) optionally one or more organic compounds that are liquid at 25° C. with a solubility parameter value δH of less than 16 $(MPa)^{1/2}$ at 25° C. as defined previously; and then, in a second step, applying to said fibres a cosmetic composition comprising:
e) optionally one or more chemical oxidizing agents chosen from hydrogen peroxide or one or more hydrogen peroxide-generating systems as defined previously; f) one or more basifying agents chosen from amino acids and (bi)carbonates, in particular alkali metal or alkaline-earth metal (bi)carbonates, alone or as a mixture;
it being understood that:
preferentially, the composition comprising a)+b)+c)+optionally d) and optionally b1) is at acidic pH, i.e. less than 7, preferably less than 5, in particular at a pH of between 1 and 3 inclusive; and
the composition comprising the basifying agent(s) is at alkaline pH, preferably of between 8 and 12 and more particularly of between 8 and 10.

For this dyeing process, the leave-on time after application for the first step is generally set at between 3 and 120 minutes, preferentially between 10 and 60 minutes and more preferentially between 15 and 45 minutes. The application time of the composition comprising the ingredient e) during the second step is generally set at between 3 and 120 minutes, preferably between 3 and 60 minutes and more preferably between 5 and 30 minutes.

According to another embodiment, the process for dyeing keratin fibres is performed in two or three steps.

According to this embodiment, the process for dyeing keratin fibres is performed in several steps by applying to the keratin fibres, in a first step, a cosmetic composition comprising:
a) one or more dyes chosen from synthetic direct dyes and dyes of natural origin, in particular one or more ODPs, especially chosen from:
haematein, brazilein, gallic acid or tannic acid, when the dyeing process does not use a chemical oxidizing agent e); or else
haematoxylin or brazilin, when the dyeing process uses a chemical oxidizing agent e);
b) one or more titanium salts as defined previously, and
b1) optionally one or more carboxylic acids of formula (I) as defined previously with A representing a monovalent $(C_1-C_6)$alkyl or polyvalent $(C_1-C_6)$alkylene group optionally substituted with one or more hydroxyl groups, and n representing an integer between 0 and 5, such as between 0 and 2, inclusive; more particularly, the carboxylic acid or acids of the invention are chosen from citric acid, lactic acid, glycolic acid and tartaric acid;
and then, in a second step, applying to said fibres a cosmetic composition comprising:
c) one or more cellulose-based polysaccharides as defined previously, which are particularly nonionic and non-associative, preferably chosen from hydroxy$(C_1-C_4)$alkylcelluloses such as hydroxyethylcelluloses (HEC);
d) optionally one or more liquid organic compounds with a Hansen solubility parameter value δH of <16 $(MPa)^{1/2}$ at 25° C., preferably chosen from aromatic alcohols such as benzyl alcohol;
e) optionally one or more chemical oxidizing agents chosen from hydrogen peroxide or one or more hydrogen peroxide-generating systems;
f) one or more basifying agent(s) chosen from amino acids, such as arginine, and (bi)carbonates, in particular alkali metal or alkaline-earth metal (bi)carbonates, alone or as mixtures;
it being understood that:
preferentially, the composition comprising a)+b) and optionally b1) is at acidic pH, i.e. less than 7, preferably less than 5, in particular at a pH of between 1 and 3 inclusive; and
the composition comprising the basifying agent(s) is at alkaline pH, preferably of between 8 and 12 and more particularly of between 8 and 10.

In particular, the dyeing process of the invention is performed in at least two steps: in the first step, ingredients a), b) and c) and optionally d) are applied together to the keratin fibres, in particular the hair, and then, in the second step, ingredients e) and f) are applied together to said fibres.

Irrespective of the application method, the application temperature is generally between room temperature (15 to 25° C.) and 220° C. and more particularly between 15 and 45° C. Thus, after application of the composition according to the invention, the head of hair may advantageously be subjected to a heat treatment by heating to a temperature of between 30 and 60° C. In practice, this operation may be performed using a styling hood, a hairdryer, an infrared ray dispenser or other standard heating appliances.

Use may be made, both as means for heating and for smoothing the head of hair, of a heating iron at a temperature of between 60° C. and 220° C. and preferably between 120° C. and 200° C.

Irrespective of the application method, it is possible to perform rinsing or mechanical wiping and/or drying of the keratin fibres between each step, in particular before performing the final step comprising the application of a composition containing the ingredient e).

The steps of intermediate mechanical wiping and drying are also known as "controlled non-rinsing" to distinguish from "standard abundant rinsing with water" and "non-rinsing". The term "mechanical wiping" of the fibres means rubbing an absorbent article on the fibres and physical removal, by means of the absorbent article, of the excess ingredient(s) that have not penetrated the fibres. The absorbent article may be a piece of fabric such as a towel, particularly a terry towel, a cloth or absorbent paper such as household roll towel.

According to a particularly advantageous process of the invention, the mechanical wiping is performed without total drying of the fibre, leaving the fibre moist.

The term "drying" means the action of evaporating the organic solvents and/or water present in one or more compositions used in the process of the invention, comprising or not comprising one or more ingredients a) to e) as defined previously. The drying may be performed with a source of heat (convection, conduction or radiation) by sending, for example, a stream of hot gas such as air necessary to evaporate the solvent(s). Sources of heat that may be mentioned include a hairdryer, a hairstyling hood, a hair-straightening iron, an infrared ray dispenser or other standard heating appliances.

A particular embodiment of the invention relates to a dyeing process which is performed at room temperature (25° C.).

In all the particular forms and variants of the processes previously described, the compositions mentioned are ready-to-use compositions that may result from the extemporaneous mixing of two or more compositions and in particular of compositions present in dyeing kits.

Dyeing Device or "Kit"

Another subject of the invention is a multi-compartment dyeing device or "kit". Advantageously, this kit comprises from 2 to 5 compartments comprising from 2 to 5 compositions in which are distributed the ingredients a) to e) as defined above, which can be aqueous or pulverulent, with in particular at least one of said compositions being aqueous.

According to a first variant, the kit comprises five compartments, the first four compartments respectively comprising ingredients a), b), c) and f) as defined previously and the fifth compartment containing an aqueous oxidizing composition, such as water comprising e) as defined previously. Optionally, d) and/or b1) are preferably contained with a).

In this other embodiment, at least one of the four compositions is aqueous and the dye(s), in particular the ODP(s), may be in powder form.

In another kit variant, this kit comprises two compartments, in which the first composition contained in the first compartment comprises a), b) and c) and the second compartment comprises e) in powder form or in aqueous medium; preferably, the second composition is aqueous.

In another kit variant, this kit comprises four compartments, in which the first composition contained in the first compartment comprises a), the second compartment comprises b), the third compartment comprises e) and the fourth compartment comprises f).

Compound c) may be in any compartment, but preferably with a). Compound d) is preferably with a), and compound b1) is preferably with b).

In another kit variant, this kit comprises three compartments, in which the first composition contained in the first compartment comprises a), the second compartment comprises e) in powder form or in aqueous medium; preferably, the second composition is aqueous and the third compartment comprises f).

Compound b) may be in any compartment, but preferably with a). Compound b) is with a) or e) and preferably with a). Compound d) is preferably with a).

According to a particular embodiment of the invention, the kit comprises five separate compartments in which the first compartment contains a) one or more dyes chosen from synthetic direct dyes and dyes of natural origin, preferably chosen from the ODPs as defined previously, the second compartment contains b) the Ti salt(s) as defined previously, and optionally b1) one or more carboxylic acids as defined previously, the third compartment contains c) one or more cellulose-based polysaccharides as defined previously, the fourth compartment contains e) one or more chemical oxidizing agents as defined previously, especially hydrogen peroxide, and a fifth compartment comprises f) one or more alkaline agents, it being understood that the solvent d) as defined previously may optionally be in at least one of the five compartments.

According to a particular embodiment of the invention, the kit comprises four separate compartments in which the first compartment contains a) one or more dyes chosen from synthetic direct dyes and dyes of natural origin, preferably chosen from the ODPs as defined previously, the second compartment contains b) the Ti salt(s) as defined previously, and optionally b1) one or more carboxylic acids as defined previously, the third compartment contains e) one or more chemical oxidizing agents as defined previously, especially hydrogen peroxide, and a fourth compartment comprises f) one or more alkaline agents, it being understood that:

c) one or more cellulose-based polysaccharides as defined previously are in at least one of the four compartments, and the solvent d) as defined previously may optionally be in at least one of the four compartments.

According to a particular embodiment of the invention, the kit comprises three separate compartments in which the first compartment contains a) one or more dyes chosen from synthetic direct dyes and dyes of natural origin, preferably chosen from the ODPs as defined previously, the second compartment contains e) one or more chemical oxidizing agents as defined previously, especially hydrogen peroxide, and a third compartment comprises f) one or more alkaline agents, it being understood that:

b) the Ti salt(s) as defined previously, and optionally b1) one or more carboxylic acids as defined previously, are with the dye(s) or with the chemical oxidizing agent(s), in particular $H_2O_2$; preferably, the Ti salt(s) are with the dye(s), c) one or more cellulose-based polysaccharides as defined previously are in at least one of the three compartments, preferably with the dye(s), and the solvent d) as defined previously may optionally be in at least one of the three compartments.

According to one variant, the device according to the invention also comprises an additional composition comprising one or more treating agents.

The compositions of the device according to the invention are packaged in separate compartments, optionally accompanied by suitable application means which may be identical or different, such as fine brushes, coarse brushes or sponges.

The device mentioned above may also be equipped with a means for dispensing the desired mixture on the hair, for instance the devices described in patent FR 2 586 913.

A subject of the invention is also the use of said cosmetic dye composition for dyeing keratin fibres.

A subject of the invention is also a cosmetic composition for dyeing keratin fibres, containing compounds a), b), b1), c), d) and e) as defined previously.

For the purposes of the present invention, the term "build-up" of the colour of keratin fibres means the variation in colouring between locks of undyed grey hair and locks of dyed hair.

The example that follows serves to illustrate the invention without, however, being limiting in nature.

EXAMPLES OF DYEING

Example 1

The following compositions are prepared from the following ingredients in the following proportions, indicated in grams per 100 grams of composition:

Dyeing Composition:

| Ingredients | Composition 1 | Composition 2 | Composition 3 |
|---|---|---|---|
| Haematoxylin, a) sold by Sigma CAS = 517-28-2 | 4 g | 4 g | 4 g |
| Dihydroxybis(ammonium lactato) titanium(IV) at 50% by weight: b) 19495-50-8 | 12.1 g | 12.1 g | 12.1 g |
| Lactic acid b1) | 10.1 g | 10.1 g | 10.1 g |
| Hydroxyethylcellulose (HEC) c) sold under the name Natrosol 250 Mr by Ashland | 1.6 g | — | — |
| HEC c) sold under the name Natrosol 250 HHR CS by Ashland | — | 1.4 g | 1.2 g |
| Ethanol | 15 g | 15 g | 15 g |
| Xanthan gum sold under the name Rhodicare XC by Rhodia | — | — | 0.4 g |
| Water | qs 100 g | qs 100 g | qs 100 g |
| pH agent | | qs pH = 2 ± 0.2 | |

Developing Composition:

| Composition B | Amount |
|---|---|
| Aqueous hydrogen peroxide solution (50%): e) | 2.4 g |
| L-Arginine: f) | 7 g |
| Sodium bicarbonate: f) | 5 g |
| Hydroxypropyl starch phosphate sold under the name Structure Zea by Akzo Nobel | 5 g |
| Water | qs 100 g |
| pH agent | pH 10 ± 0.3 |

The dye compositions 1 to 3 and then composition B are applied with a brush to permanent-waved Caucasian hair containing 90% white hairs.

Compositions 1 to 3 are then left on for a time of 45 minutes at 40° C. and composition B is left on for a time of 15 minutes at 40° C. Rinsing is performed before applying composition B.

After these leave-on times, the locks are washed with Elvive Multivitamin shampoo, rinsed and then dried under a hood.

Dyeing Results

It is found that very strongly coloured black locks are obtained, which is corroborated by the colorimetric measurements below. In addition, it is seen that the colouring is visually homogeneous and persistent with respect to successive shampooing.

The colour of the locks was evaluated in the CIE $L^*a^*b^*$ system using a Minolta Spectrophotometer CM3600D colorimeter. In this $L^*a^*b^*$ system, the three parameters denote, respectively, the colour intensity ($L^*$), the green/red colour axis ($a^*$) and the blue/yellow colour axis ($b^*$).

Colour Build-Up:

The variation in colouring between the locks of permanent-waved Caucasian hair containing 90% white hairs, before and after treatment or dyeing, is defined by ($\Delta E^*$) according to the following equation:

$$\Delta E^* = \sqrt{(L^*-L_o^*)^2+(a^*-a_o^*)^2+(b^*-b_o^*)^2}$$

In this equation, $L^*$, $a^*$ and $b^*$ represent the values measured on locks of hair after dyeing and $L_o^*$, $a_o^*$ and $b_o^*$ represent the values measured on locks of undyed virgin hair. The higher the $\Delta E^*$ value, the better the colour build-up.

The results L, a, b of colour build-up are collated in the table below:

| Types of hair and treatment | Colour | $L^*$ | $a^*$ | $b^*$ | $\Delta E^*$ build-up |
|---|---|---|---|---|---|
| Composition 1 then B | | | | | |
| Natural permanent-waved Caucasian, 90% white hairs | Black | 22.16 | 1.97 | 2.39 | 42.9 |
| Composition 2 then B | | | | | |
| Natural permanent-waved Caucasian, 90% white hairs | Black | 21.99 | 2.32 | 2.51 | 43.04 |
| Composition 3 then B | | | | | |
| Natural permanent-waved Caucasian, 90% white hairs | Black | 21.16 | 1.88 | 1.86 | 44.01 |

After the keratin fibres have been treated with compositions 1 to 3, the locks obtained are a very strong and intense black.

Example 2

The following dye compositions are prepared according to the same protocol as in Example 1:

Dyeing Composition:

| Ingredients | Composition 4 | Composition 5 |
|---|---|---|
| Disperse Red 13, a) 3180-81-2 | 0.5 g | — |
| HC Violet 2: 2-N-hydroxypropylamino-5-N,N-bis(b-hydroxyethyl)aminonitrobenzene a) | — | 0.5 g |
| Glycolic acid b1) | 15 g | 15 g |
| Dihydroxybis(ammonium lactato) titanium(IV) at 50% by weight: b) | 10.3 g | 10.3 g |
| HEC sold under the name Natrosol 250 HHR CS by Ashland, c) | 1.2 g | — |
| HEC sold under the name Natrosol 250 Mr by Ashland, c) | — | 1 g |
| Ethanol | 15 g | 15 g |
| Benzyl alcohol d) | 5 g | 5 g |
| Water | qs 100 g | qs 100 g |
| pH agent | qs pH = 2 ± 0.2 | |

Very strongly coloured red locks (composition 4) and violet locks (composition 5) are obtained.

The invention claimed is:

1. A method for dyeing keratin fibers, comprising applying to the fibers:
   a) at least one dye chosen from synthetic direct dyes and/or dyes of natural origin;
   b) at least one organic titanium salt, wherein the organic titanium salt is chosen from compounds according to formula (I-A) below:

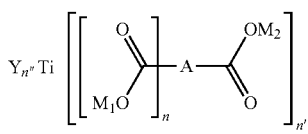 (I-A)

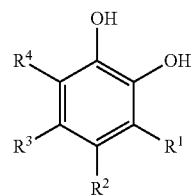 (II)

wherein:
A is chosen from a monovalent group when n is 0 or a polyvalent group when n is greater than or equal to 1; or a saturated or unsaturated, cyclic or non-cyclic and aromatic or non-aromatic hydrocarbon-based group comprising from 1 to 50 carbon atoms which is optionally interrupted with at least one heteroatom and/or optionally substituted;

n, n', and n" may be identical or different, n is an integer ranging from 0 to 4, n' and n" are integers chosen from 1, 2, 3, or 4, wherein n'+n"=6;

$M_1$ and $M_2$, which may be identical or different, are chosen from a cationic counterion; and $TiY_{n''}$ is chosen from $Ti(OH)_{n''}$, $Ti(O)_{n''/2}$, or $Ti(OH)_{m1}(O)_{m2}$ with $m_1+m_2=n''$;

b1) at least one carboxylic acid according to formula (I) below, or salts thereof:

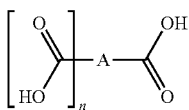 (I)

wherein:
A is chosen from a monovalent ($C_1$-$C_6$)alkyl groups or polyvalent ($C_1$-$C_6$)alkylene groups optionally substituted with at least one hydroxyl group; and n is an integer ranging from 0 to 5;

c) at least one cellulose-based polysaccharide, wherein the at least one cellulose-based polysaccharide is chosen from associative or non-associative anionic, cationic, amphoteric, or nonionic polymers;

d) optionally, at least one organic compound that is liquid at 25° C. with a Hansen solubility parameter value δH of less than 16 (MPa)$^{1/2}$ at 25° C.; and e) optionally, at least one chemical oxidizing agent chosen from hydrogen peroxide or at least one hydrogen peroxide-generating system.

2. The method according to claim 1, wherein the at least one dye is an ortho-diphenol comprising an aromatic ring, wherein the aromatic ring is chosen from benzene, naphthalene, tetrahydronaphthalene, indane, indene, anthracene, phenanthrene, isoindole, indoline, isoindoline, benzofuran, dihydrobenzofuran, chroman, isochroman, chromene, isochromene, quinoline, tetrahydroquinoline, or isoquinoline, wherein the aromatic ring comprises at least two hydroxyl groups borne by two contiguous adjacent atoms of the aromatic ring.

3. The method according to claim 1, wherein the at least one dye is an ortho-diphenol according to formula (II) below, oligomers, tautomers, optical isomers, geometrical isomers thereof, salts, solvates, or hydrates thereof:

wherein:
$R^1$ to $R^4$, which may be identical or different, are chosen from: i) hydrogen, ii) halogen atoms, iii) hydroxyl groups, iv) carboxyl groups, v) ($C_1$-$C_{20}$) alkyl carboxylate or ($C_1$-$C_{20}$)alkoxycarbonyl groups, vi) optionally substituted amino groups, vii) optionally substituted linear or branched ($C_1$-$C_{20}$)alkyl groups, viii) optionally substituted linear or branched ($C_2$-$C_{20}$)alkenyl groups, ix) optionally substituted cycloalkyl groups, x) ($C_1$-$C_{20}$)alkoxy groups, xi) ($C_1$-$C_{20}$)alkoxy($C_1$-$C_{20}$)alkyl groups, xii) ($C_1$-$C_{20}$) alkoxyaryl groups, xiii) aryl groups which may optionally be substituted, xiv) aryl groups, xv) substituted aryl groups, xvi) heterocyclic groups which are saturated or unsaturated, optionally bearing a cationic or anionic charge and which are optionally substituted and/or optionally fused with an aromatic ring, the aromatic ring optionally substituted, or xvii) radical groups containing at least one silicon atom;

or, optionally:
two of the substituents borne by two adjacent carbon atoms $R^1$-$R^2$, $R^2$-$R^3$ or $R^3$-$R^4$ optionally form, together with the carbon atoms bearing them, a saturated or unsaturated, aromatic or non-aromatic ring optionally containing at least one heteroatom and optionally fused with at least one saturated or unsaturated ring optionally containing at least one heteroatom;

$R^1$ to $R^4$ together form from one to four rings; or
$R^2$ and $R^3$ form a pyrrolyl or pyrrolidinyl radical fused to the benzene ring bearing the two hydroxyls.

4. The method according to claim 1, wherein the at least one dye is an ortho-diphenol chosen from:
flavanols;
anthocyanidins;
anthocyanins or anthocyans;
ortho-hydroxybenzoates;
flavones;
hydroxystilbenes;
3,4-dihydroxyphenylalanine or derivatives thereof;
2,3-dihydroxyphenylalanine or derivatives thereof;
4,5-dihydroxyphenylalanine or derivatives thereof;
dihydroxycinnamates;
ortho-polyhydroxycoumarins;
ortho-polyhydroxyisocoumarins;
ortho-polyhydroxycoumarones;
ortho-polyhydroxyisocoumarones;
ortho-polyhydroxychalcones;
ortho-polyhydroxychromones;
quinones;
hydroxyxanthones;
1,2-dihydroxybenzene or derivatives thereof;
1,2,4-trihydroxybenzene or derivatives thereof;
1,2,3-trihydroxybenzene or derivatives thereof;
2,4,5-trihydroxytoluene or derivatives thereof;

proanthocyanidins;
chromans or chromenes;
proanthocyanins;
tannic acid;
ellagic acid;
or mixtures thereof.

5. The method according to claim 1, wherein the at least one dye is an ortho-diphenol chosen from extracts of animals, bacteria, fungi, algae, plants, or fruit.

6. The method according to claim 1, wherein the at least one carboxylic acid is present in an amount ranging from about 0.1% to about 20% by weight, relative to the total weight of the composition.

7. The method according to claim 1, wherein the organic titanium salts are dihydroxybis(lactato)titanium(IV) salts according to the formula below:

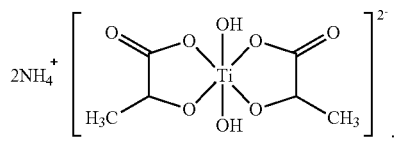

8. The method according to claim 1, wherein the composition comprises at least one organic compound chosen from organic solvents, such organic solvents chosen from:
propylene glycol derivatives;
aromatic alcohols;
alkylene carbonates;
lactones according to formula (D1) below:

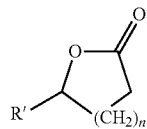

(D1)

wherein:
n is equal to 1, 2 or 3; and
R' is chosen from hydrogen atom; a linear or branched $C_1$-$C_8$ alkyl radical; or a linear or branched $C_1$-$C_4$ hydroxyalkyl radical;
alcohols;
ethers;
or mixtures thereof.

9. The method according to claim 1, wherein the composition comprises at least one organic compound chosen from alcohols, aromatic alcohols, benzyl alcohol, ethers, propylene glycol derivatives, or mixtures thereof.

10. The method according to claim 1, wherein the composition comprises at least one chemical oxidizing agent chosen from hydrogen peroxide or at least one hydrogen peroxide-generating system.

11. The method according to claim 1, further comprising applying at least one basifying agent to the hair, said basifying agent chosen from: i) (bi)carbonates; ii) aqueous ammonia; iii) alkanolamines; iv) oxyethylenated and/or oxypropylenated ethylenediamines; v) mineral or organic hydroxides; vi) alkali metal silicates; vii) amino acids; or viii) the compounds according to formula (XIII) below:

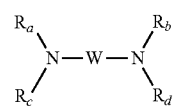

(XIII)

wherein:
W is a divalent ($C_1$-$C_8$)alkylene radical optionally substituted with at least one hydroxyl group or at least one ($C_1$-$C_4$)alkyl radical and/or optionally interrupted with at least one heteroatomor with a group —N($R_e$)—; and
$R_a$, $R_b$, $R_c$, $R_d$, and $R_e$, which may be identical or different, are chosen from hydrogen, a ($C_1$-$C_4$)alkyl or hydroxy($C_1$-$C_4$)alkyl radical, or mixtures thereof.

12. The method according to claim 1, wherein the composition has a pH of less than 7.

13. The method according to claim 1, comprising:
applying to the keratin fibers
a) at least one dye chosen from synthetic direct dyes and/or dyes of natural origin;
b) at least one organic titanium salt, wherein the organic titanium salt is chosen from compounds according to formula (I-A) below:

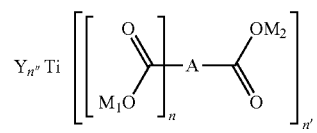

(I-A)

wherein:
A is chosen from a monovalent group when n is 0 or a polyvalent group when n is greater than or equal to 1; or a saturated or unsaturated, cyclic or non-cyclic and aromatic or non-aromatic hydrocarbon-based group comprising from 1 to 50 carbon atoms which is optionally interrupted with at least one heteroatom and/or optionally substituted;
n, n', and n" may be identical or different, n is an integer ranging from 0 to 4, n' and n" are integers chosen from 1, 2, 3, or 4, wherein n'+n"=6;
$M_1$ and $M_2$, which may be identical or different, are chosen from a cationic counterion; and
$TiY_{n''}$ is chosen from $Ti(OH)_{n''}$, $Ti(O)_{n''/2}$, or $Ti(OH)_{m_1}(O)_{m_2}$ with $m_1+m_2=n''$;
b1) at least one carboxylic acid according to formula (I) below, or salts thereof:

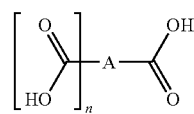

(I)

wherein:
A is chosen from monovalent ($C_1$-$C_6$)alkyl groups or polyvalent ($C_1$-$C_6$)alkylene groups optionally substituted with at least one hydroxyl group; and
n is an integer ranging from 0 to 5;
c) at least one cellulose-based polysaccharide, wherein the at least one cellulose-based polysaccharide is chosen from associative or non-associative anionic, cationic, amphoteric, or nonionic polymers; and
d) optionally, at least one organic compound that is liquid at 25° C. with a Hansen solubility parameter value δH of less than 16 (MPa)$^{1/2}$ at 25° C.;
wherein the dyeing composition has a pH of less than 7; and
e) optionally, at least one chemical oxidizing agent chosen from hydrogen peroxide or at least one hydrogen peroxide-generating system; and
f) at least one basifying agent;
wherein the alkaline composition has a pH greater than 7.

14. A cosmetic composition for dyeing keratin fibers, comprising:
a) at least one dye chosen from synthetic direct dyes and/or dyes of natural origin;
b) at least one organic titanium salt, wherein the organic titanium salt is chosen from compounds according to formula (I-A) below:

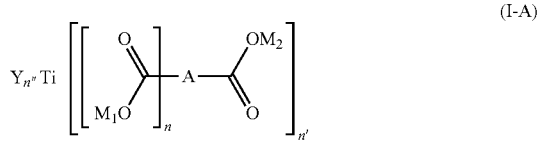

wherein:
A is chosen from a monovalent group when n is 0 or a polyvalent group when n is greater than or equal to 1; or a saturated or unsaturated, cyclic or non-cyclic and aromatic or non-aromatic hydrocarbon-based group comprising from 1 to 50 carbon atoms which is optionally interrupted with at least one heteroatom and/or optionally substituted;
n, n', and n" may be identical or different, n is an integer ranging from 0 to 4 n' and n" are integers chosen from 1, 2, 3, or 4, wherein n'+n"=6;
$M_1$ and $M_2$, which may be identical or different, are chosen from a cationic counterion; and
$TiY_{n''}$ is chosen from $Ti(OH)_{n''}$, $Ti(O)_{n''/2}$, or $Ti(OH)_{m_1}(O)_{m_2}$ with $m_1+m_2=n''$;
b1) at least one carboxylic acid according to formula (I) below, or salts thereof:

wherein:
A is chosen from a monovalent ($C_1$-$C_6$)alkyl groups or polyvalent ($C_1$-$C_6$)alkylene groups optionally substituted with at least one hydroxyl group; and
n is an integer ranging from 0 to 5;
c) at least one cellulose-based polysaccharide, wherein the at least one cellulose-based polysaccharide is chosen from associative or non-associative anionic, cationic, amphoteric, or nonionic polymers;
d) optionally, at least one organic compound that is liquid at 25° C. with a Hansen solubility parameter value δH of less than 16 (MPa)$^{1/2}$ at 25° C.; and e) optionally, at least one chemical oxidizing agent chosen from hydrogen peroxide or at least one hydrogen peroxide-generating system.

15. A multi-compartment device comprising from 2 to 5 compartments containing from 2 to 5 compositions, the device comprising:
a) at least one dye chosen from synthetic direct dyes and/or dyes of natural origin;
b) at least one organic titanium salt, wherein the organic titanium salt is chosen from compounds according to formula (I-A) below:

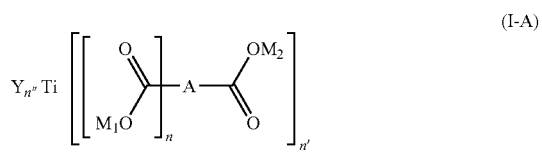

wherein:
A is chosen from a monovalent group when n is 0 or a polyvalent group when n is greater than or equal to 1; or a saturated or unsaturated, cyclic or non-cyclic and aromatic or non-aromatic hydrocarbon-based group comprising from 1 to 50 carbon atoms which is interrupted with at least one heteroatom and/or optionally substituted;
n, n', and n" may be identical or different, n is an integer ranging from 0 to 4, n' and n" are integers chosen from 1, 2, 3, or 4, wherein n'+n"=6;
$M_1$ and $M_2$, which may be identical or different, are chosen from a cationic counterion; and
$TiY_n$ is chosen from $Ti(OH)_{n''}$, $Ti(O)_{n''/2}$, or $Ti(OH)_{m_1}(O)_{m_2}$ with $m_1+m_2=n''$;
b1) at least one carboxylic acid according to formula (I) below, or salts thereof:

wherein:
A is chosen from a monovalent ($C_1$-$C_6$)alkyl groups or polyvalent ($C_1$-$C_6$)alkylene groups optionally substituted with at least one hydroxyl group; and
n is an integer ranging from 0 to 5;
c) optionally, at least one cellulose-based polysaccharide, wherein the at least one cellulose-based polysaccharide is chosen from associative or non-associative anionic, cationic, amphoteric, or nonionic polymers;
d) optionally, at least one organic compound that is liquid at 25° C. with a Hansen solubility parameter value δH of less than 16 (MPa)$^{1/2}$ at 25° C.; and
e) optionally, at least one chemical oxidizing agent chosen from hydrogen peroxide or at least one hydrogen peroxide-generating system;
wherein at least one compartment further comprises water.

* * * * *